United States Patent [19]
Itoh et al.

[11] Patent Number: 5,594,144
[45] Date of Patent: Jan. 14, 1997

[54] TROPOLONE DERIVATIVES AND PHARMACEUTICAL COMPOSITION THEREOF FOR PREVENTING AND TREATING ISCHEMIC DISEASES

[75] Inventors: Noriie Itoh, Ami-machi; Mineo Kunihara, Tsukuba; Hiroshi Kushida, Shimodate, all of Japan; William W. McWhorter, Parchment, Mich.; Syunji Nomura, Tsukuba, Japan; Kazunori Ozawa, Tsukuba, Japan; Mikio Taniguchi, Tsukuba, Japan; Kazuo Tsuzuki, Tsukuba, Japan

[73] Assignee: The Upjohn Company, Kalamazoo, Mich.

[21] Appl. No.: 442,710

[22] Filed: May 18, 1995

Related U.S. Application Data

[62] Division of Ser. No. 975,924, filed as PCT/US91/05906, Aug. 27, 1991, abandoned.

[30]    Foreign Application Priority Data

Aug. 29, 1990  [JP]  Japan .................... 2-229536
Jan. 31, 1991  [JP]  Japan .................... 3-056252
Feb. 8, 1991  [JP]  Japan .................... 3-039173

[51] Int. Cl.$^6$ .................... C07D 277/66; C07D 401/10; A61K 31/425; A61K 31/445
[52] U.S. Cl. .................... 548/166; 548/180; 546/199; 544/135; 544/369
[58] Field of Search .................... 548/180, 166; 546/199; 544/135, 369; 514/367, 255, 326, 233.8

[56]    References Cited

FOREIGN PATENT DOCUMENTS 0034894  9/1981  European Pat. Off. .
0400974  12/1990  European Pat. Off. .

OTHER PUBLICATIONS

Chemical Abstracts, vol. 79, No. 11, 17 Sep. 1973, Hikaru Ozawa, #61705m 1973.
Chemical Abstracts, vol. 77, No. 15, 9 Oct. 1972, Hikaru Ozawa, #96876d 1972.
Chemical Abstracts, vol. 76, No. 25, 19 Jun. 1972, Hikaru Ozawa, #149003e 1972.
Banner, Perspect. Mach. Chem., pp. 27–43, 1993 1993.
Shuman, J. Med. Chem., vol. 36, pp. 314–319, 1993 1993.

*Primary Examiner*—C. Warren Ivy
*Assistant Examiner*—D. Margaret Mach
*Attorney, Agent, or Firm*—Lawrence T. Welch

[57]    ABSTRACT

The present invention provides novel tropolone derivatives of the formula I

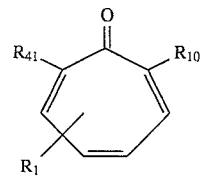

wherein $R_{10}$ is a substituted or unsubstituted piperazinyl or benzothiazolidinyl group, and pharamaceutical compositions thereof. These compounds are useful for the prevention and treatment of ischemic diseases, including cerebrovascular diseases and cardiovascular diseases.

3 Claims, No Drawings

TROPOLONE DERIVATIVES AND PHARMACEUTICAL COMPOSITION THEREOF FOR PREVENTING AND TREATING ISCHEMIC DISEASES

The present application is a division of U.S. Ser. No. 07/975,924, filed Feb. 18, 1993, now abandoned; which is the National Stage of International Application PCT/US91/05906, filed Aug. 27, 1991; which claims the benefit of Japanese Application No. 056252/1991, filed Jan. 31, 1991; Japanese Application No. 039173/1991, filed Feb. 8, 1991; and Japanese Application No. 229536/1990, filed Aug. 29, 1990.

FIELD OF THE INVENTION

The present invention relates to novel compounds and novel pharmaceutical compositions containing them for preventing or treating ischemic diseases. Particularly, the present invention provides tropolone derivatives or a pharmaceutically acceptable esters or salts thereof and compositions containing them as an active ingredient. More particularly, it relates to a preventive or a remedy for cerebrovascular diseases such as cerebral hemorrhage, cerebral infarction, subarachnoid hemorrhage, transient ischemic attacks (TIA), trauma, the sequelae associated with brain surgery, or cardiovascular diseases such as variant angina pectoris, unstable angina, myocardial infarction, arrhythmia caused upon reflowing of coronary blood stream after procedures such as Percutaneous Transluminal Coronary Angioplasty/Percutaneous Transluminal Coronary Recanalization/Coronary Artery Bypass Grafting (PTCA/PTCR/CABG) and the like.

BACKGROUND OF THE INVENTION

Cellular disorders due to ischemia mainly comprise two disorder stages, that is, (1) a stage which proceeds under anoxic/hypoxic conditions and (2) a process of injury by active oxygen inevitably generated in the course of ischemia/reperfusion [see Nishida et at., Metabolism, vol. 24, 379 (1987)]. The typical ischemic diseases include, for example, cerebrovascular diseases such as cerebral hemorrhage, cerebral infarction, subarachnoid hemorrhage, transient ischemic attach (TIA), trauma, the sequelae associated with brain surgery, or cardiovascular diseases such as variant angina pectoris, unstable angina, myocardial infarction, arrhythmia caused upon reflowing of coronary blood stream by PTCA/PTCR/CABG and the like. Further, disorders of transplanted organs upon organ transplantation, disorders of organs caused by decreased blood flow after shock, temporary devascularization of an organ during a surgical operation and the like. These diseases are difficult to be explained with a single mechanism, and it is considered to be caused by complicatedly related factors. In clinical practice, various medicines are selected for the particular causes and conditions. For example, as a preventive and a remedy for cerebrovascular diseases, Glyceol, Ozagrel, Nizofenone, Ticlopidine, AVS and the like are used and studied for the acute stage from the viewpoint of prevention of brain edema and cerebrovascular contraction. On the other hand, in the chronic stage, cerebral circulation improvers such a nicardipine, cinnarizine, flunarizine, dilazep; cerebral circulation metabolism improvers such as vinpocetine, Nicergoline, pentoxifylline, and ifenprodil; and cerebral metabolism improvers such as Idebenone, GABA, and calcium hopatenate have been used. For variant angina pectoris and unstable angina, vasodilators such as nitro compound, and calcium (Ca) antagonists have been used. For myocardial infarction, cardiac disorder upon reflowing of coronary blood by PTCA/PTCR/CABG and the like, 5-lipoxygenase inhibitors and radical scavengers have been investigated, but, no medicines with a clinically satisfactory result have been found.

PROBLEMS TO BE SOLVED BY THE INVENTION

The present inventors have thought that such ischemic diseases are caused by disorder of cell membrane or tissue by active oxygen and excessive and sudden flow of extracellular calcium ion into the cell, said two causes being closely related to each other. That is, when a disorder of cell membrane is caused by active oxygen, extracellular calcium flows into the cell. Accordingly, an amplification reaction may proceed, wherein protease in the cell is activated, resulting in deactivation of function as a cell, or phospholipase is activated to decompose the ingredients of the cell membrane, resulting in further inflow of calcium. Arachidonic acid separated out from ingredients of a cell membrane by activation of phospholipase may be metabolized and convened into a material which derives phagocytes (e.g., leukotrienes) or a material which coagulates blood plates to produce thrombus (e.g., thromboxane $A_2$). Further, it produces active oxygen again in this conversion step. Accordingly, the diseases may become worse.

From such a point of view, the present inventors have studied intensively medicines which are effective for prevention and cure of ischemic diseases. As the result, we have found that a certain kind of novel tropolone derivative is effective. Thus, we have attained the present invention.

MEANS TO SOLVE THE PROBLEMS

The present invention particularly provides:
(1.) A tropolone derivative of the formula:

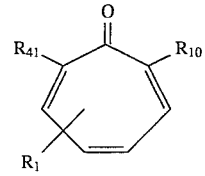

wherein $R_{10}$ is a moiety of the formula II or III

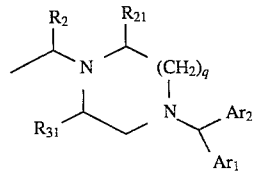

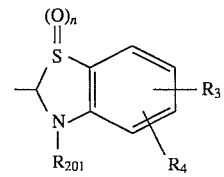

wherein $R_1$ and $R_2$ are the same or different and are:
(a) hydrogen,
(b) $C_1$–$C_5$ alkyl,
(c) substituted or non-substituted aryl, or (d) a substituted or non-substituted heterocyclic group;
wherein $R_3$ and $R_4$ are the same or different and are:
(a) hydrogen,
(b) $C_1-C_5$ alkyl,
(c) $C_1-C_5$ alkyl substituted by —OH, —COOR$_5$, or —CN,
(d) $C_7-C_{20}$ arylalkyl,
(e) $C_7-C_{20}$ arylalkyl containing O, S or N as heteroatoms,
(f) halogen,
(g) —OH,
(h) $C_1-C_5$ alkoxy,
(i) —CN,
(j) —CO$_2$R$_5$, or
(k) —NO$_2$;
wherein $R_{41}$ is
(a) —OR$_3$,
(b) —OR$_6$,
(c) —NR$_7$R$_8$,
(d) —N(R$_{51}$)—(CH$_2$)$_m$—R$_{61}$, or
(e) a group represented by the formula IV

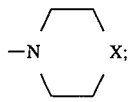

wherein $R_5$ is
(a) hydrogen, or
(b) $C_1-C_5$ alkyl;
wherein $R_6$ is
(a) hydrogen,
(b) $C_1-C_5$ alkyl,
(c) $C_1-C_5$ alkyl substituted by OH, COOR$_5$, or CN,
(d) $C_7-C_{20}$ aralkyl, or
(e) $C_7-C_{20}$ aralkyl substituted by O, S or N;
wherein $R_7$ and $R_8$ are the same or different and are:
(a) hydrogen,
(b) $C_1-C_5$ alkyl,
(c) $C_1-C_5$ alkyl substituted by —OH, —COOR$_5$, or —CN, or containing O, S, or N as heteroatoms,
(d) $C_7-C_{20}$ aralkyl,
(e) $C_7-C_{20}$ aralkyl containing O, S or N as heteroatoms, or
(f) $R_7$ and $R_8$ together form a 5 to 7 membered ring may contain 1–3 of the following ring substituents;
(i) —CH$_2$—,
(ii) —O—, or
(iii) —NR$_9$—;
wherein $R_9$ is
(a) hydrogen,
(b) $C_1-C_5$ alkyl, or
(c) $C_7-C_{20}$ aralkyl, or
(d) $C_7-C_{20}$ aralkyl containing O, S or N as heteroatoms;
wherein $R_{11}$ is
(a) hydrogen,
(b) $C_1-C_3$ alkyl,
(c) substituted or unsubstituted aryl, or
(d) substituted or unsubustituted heterocycle;
wherein $R_{21}$ and $R_{31}$ are the same or different and are
(a) hydrogen, or (b) $C_1-C_3$ alkyl;
wherein $R_{61}$ is
(a) substituted or unsubstituted aryl,
(b) substituted or unsubstituted heterocycle,
(c) —OR$_{71}$,
(d) —CO$_2$R$_{81}$, or
(e) —NR$_{91}$R$_{101}$;
wherein $R_{51}$, $R_{71}$, and $R_{81}$ are the same or different and are
(a) hydrogen, or
(b) $C_1-C_3$ alkyl;
wherein $R_{91}$ and $R_{101}$ are the same or different and are
(a) hydrogen,
(b) $C_1-C_3$ alkyl,
(c) a substituted or unsubstituted aryl group, or
(d) a substituted or unsubstituted heterocycle;
wherein $R_{201}$ is
(a) hydrogen,
(b) $C_1-C_5$ alkyl,
(c) $C_2-C_{20}$ aralkyl,
(d) $C_6-C_{10}$ arylsulfonyl, or
(e) $C_6-C_{10}$ arylsulfonyl containing O, S, or N as additional heteroatoms;
wherein $Ar_1$ and $Ar_2$ are the same or different aryl group optionally substituted by
(a) halogen,
(b) trihalomethyl,
(c) $C_6-C_{10}$ aryl, or
(d) $C_6-C_{10}$ aryl substituted by $C_1-C_3$ alkoxy;
wherein X is
(a) —O—,
(b) —CH$_2$—, or
(c) —N—(CH$_2$)$_p$—R$_{11}$;
wherein m is 1, 2, 3, or 4;
wherein n is 0, 1, or 2;
wherein p is 0, 1, or 2; and
wherein q is 1 or 2;
or a pharmaceutically acceptable ester or salt thereof;
(2.) A tropolone derivative as described in (1) wherein $R_{41}$ is OR$_3$ (wherein $R_3$ is definitions (a) to (e)), $R_{10}$ is a moiety of the Formula II, $R_{21}$ and $R_{31}$ are hydrogen and q is 1, represented by the formula:

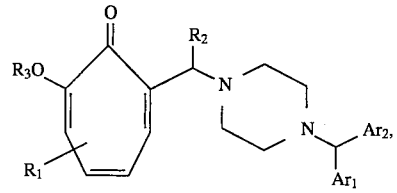

or a pharmaceutically acceptable ester or salt thereof;

(3.) A tropolone derivative as described in (1), wherein $R_{41}$ is —$OR_6$ or —$NR_7R_8$, $R_{10}$ is a moiety of Formula III, $R_1$ is definitions (a) to (c), $R_3$ and $R_4$ are definitions (a), (b), and (f) to (k), represented by the formula:

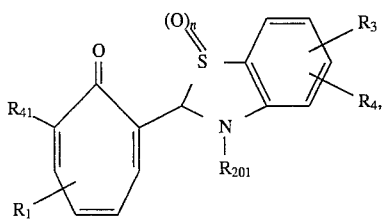

IB or a pharmaceutically acceptable ester or salt thereof;

(4.) A tropolone derivative as described in (1), wherein $R_{41}$ is —$N(R_{51})$—$(CH_2)_m$—$R_{61}$ or a group of the Formula IV; $R_{10}$ is a group of the Formula II, represented by the formula:

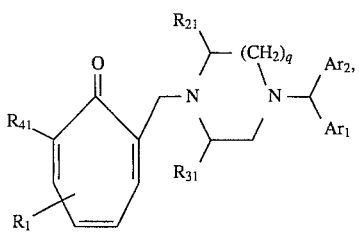

IC or a pharmaceutically acceptable ester or salt thereof; and (5.) A pharmaceutical composition for preventing or treating ischemic diseases which is characterized by containing a tropolone derivative described above or a pharmaceutically acceptable ester or salt thereof as an active ingredient.

The carbon atom content of the various hydrocarbon containing moieties is indicated by, e.g., "$C_i$–$C_j$," wherein i is the minimum number of carbon atoms and j is the maximum number of carbon atoms.

In the compound of the present invention represented by the general formula [I], a lower alkyl group represented by $R^1$ and $R^2$ includes, for example, $C_{1-5}$ alkyl group such as methyl, ethyl, n-propyl, isopropyl, n-butyl, isobutyl, n-pentyl, isoamyl. An aryl group includes, for example, $C_{6-10}$ aryl which may contain 1 to 7 substitutents selected from a group consisting of the aforementioned lower alkyl group, halogen, nitro, cyano, lower alkoxy group. Such halogen includes chloro, fluoro, bromo and iodo; and lower alkoxy group includes a $C_{1-5}$ alkoxy group. The example of these aryl groups includes, for example, phenyl, p-chlorophenyl, m-chlorophenyl, o-chlorophenyl, o,m-dichlorophenyl, p-fluorophenyl, p-trifluorophenyl, p-nitrophenyl, m-nitrophenyl, o-nitrophenyl, p-cyanophenyl, m-cyanophenyl, o-cyanophenyl, p-methoxyphenyl, m-methoxyphenyl, o-methoxyphenyl, m,p-dimethoxyphenyl. A heterocyclic group includes a 5–10 membered heterocyclic group containing at least one hetero atom. These may be substituted with substitutents similar to those in the above aryl group. Examples of such heterocyclic group includes 2-pyridyl, 3-pyridyl, and 4-pyridyl.

A lower alkyl group represented by $R^3$ which may be substituted by hetero atoms includes $C_{1-20}$ alkyl group substituted by amino, mono- or di-substituted amino group substituted by substituted or non-substituted aralkyl, lower alkyl group or substituted/non-substituted aralkyl group, or hydroxyl group. A lower alkyl group as a substituent includes $C_{1-5}$ alkyl, and an aralkyl group includes $C_{7-20}$ aralkyl group which may be substituted by the substitutent similar to those in the above aryl group. The example of such lower alkyl group which may be substituted by hetero atom includes, for example, methyl, ethyl, n-propyl, n-butyl, 2-[N,N-dimethylamino]ethyl, 3-[N,N-dimethylamino]propyl, 2-[N-methyl-N-phenethylamino]ethyl, 3-[N-methyl-N-phenethylamino]propyl, 2-[N-methyl-N-2,3-dimethoxyphenethylamino]ethyl, 3-[N-methyl-N-2,3-dimethoxyphenethylamino]propyl, 2-hydroxyethyl, 3-amino-2-hydroxypropyl, 3-dimethylamino-2-hydroxypropyl, 3-diisopropylamino-2-hydroxypropyl. An aralkyl group includes $C_{7-20}$ aralkyl group which may be substituted by a substitutent similar to those in the above aryl group, (e.g., containing O, S, or N as heteroatoms) for example, benzyl, phenethyl, 3,4-dimethoxyphenethyl, 2,3,4-trimethoxyphenethyl.

Aryl groups represented by $Ar^1$ and $Ar^2$ include those similar to the aryl groups represented by $R^1$ and $R^2$, for example, phenyl, p-chlorphenyl, m-chlorphenyl, o-chlorphenyl, o,m-dichlorphenyl, o,p-dichlorphenyl, m,p-dichlorphenyl, p-fluorophenyi, m-fluorophenyl, o-fluorophenyl, p-trifluorophenyl, m-trifluorophenyl, o-trifluorophenyl, p-methoxyphenyl, m-methoxyphenyl, o-methoxyphenyl.

An arylsulfonyl group in which a constituent may be substituted by a heteroatom includes $C_6$-$C_{10}$ arylsulfonyl containing at least one heteroatom selected from the group consisting of N, S and O. These may be subjected to nuclear substitution by substituents similar to those in the above aromatic group. Examples thereof include, for example, phenylsulfonyl, naphthylsulfonyl, quinolylsulfonyl, and isoquinolylsulfonyl.

A pharmaceutically acceptable salt of the tropolone derivative of the present invention represented by the general formula [I] includes a salt with a mineral acid such as hydrochloric acid, sulfuric acid; a salt with an organic sulfonic acid such as methanesulfonic acid, p-toluenesulfonic acid; a salt with an organic carboxylic acid such as acetic acid, propionic acid, succinic acid, lactic acid, tartaric acid, malic acid, citric acid and the like. An ester thereof includes an ester with an organic carboxylic acid such as acetic acid, propionic acid, oxalic acid and the like.

The embodiments of the compound of the present invention represented by the general formula [IA] are shown below:

1A) 7-[4-(4-chlorobenzhydryl)piperazino-1-methyl]-2-hydroxy4-isopropyl-2,4,6-cycloheptatrien-1-one;

2A) 7-[4-(4-chlorobenzhydryl)piperazino-1-methyl]-4-isopropyl-2-methoxy-2,4,6-cycloheptatrien-1-one;

3A) 7-{1-[4-(4-chlorobenzhydryl)piperazinomethyl]-α-phenyl}-4-isopropyl-2-methoxy-2,4,6-cycloheptatrien-1-one;

4A) 7-{1-[4-(4-chlorobenzhydryl)]piperazinomethyl-α-methyl-}-4-isopropyl-2-methoxy-2,4,6-cycloheptatrien-1-one;

5A) 7-{1-[4-(4-chlorobenzhydryl)]piperazinomethyl]-α-butyl}-4-isopropyl-2-methoxy-2,4,6-cycloheptatrien-1-one;

6A) 7-(4-benzhydrylpiperazino-1-methyl)-4-isopropyl-2-methoxy-2,4,6-cycloheptatrien-1 -one;

7A) 7-[4-(4,4'-difluorobenzhydryl)piperazino-1-methyl]-4-isopropyl-2-methoxy-2,4,6-cycloheptatrien-1-one;

8A) 7-{4-[4,4'-di(trifluoromethyl)benzhydryl]piperazino-1-methyl}-4-isopropyl-2-methoxy-2,4,6-cycloheptatrien-1-one;

9A) 4-isopropyl-2-methoxy-7-[4-(4-trifluoromethylbenzhydryl)piperazino-1-methyl]-2,4,6-cycloheptatrien-1-one;

10A) 7-[4-(4-chloro-4'-methoxybenzhydryl)piperazin-1-methyl]-4-isopropyl-2-methoxy-2,4,6-cycloheptatrien-1-one;

11A) 7-[4-(4-fluoro-3',4'-dimethoxybenzhydryl)piperazino-1-methyl]-4-isopropyl-2-methoxy-2,4,6-cycloheptatrien-1-one;

12A) 7-[4-(4,4'-difluorobenzhydryl)piperazino-1-methyl]-2-ethoxy-4-isopropyl-2,4,6-cycloheptatrien-1-one;

13A) 2-butoxy-7-[4-(4,4'-difluorobenzhydryl)piperazino-1-methyl]-4-isopropyl-2,4,6-cycloheptatrien-1-one;

14A) 7-[4-(4,4'-difluorobenzhydryl)piperazino-1-methyl]-4-isopropyl-2-phenoxy-2,4,6-cycloheptatrien-1-one;

15A) 2-benzyloxy-7-[4-(4,4'-difluorobenzhydryl)piperazino-1-methyl]-4-isopropyl-2,4,6-cycloheptatrien-1-one;

16A) 7-[4-(4,4'-difluorobenzhydryl)piperazino-1-methyl]-2-[2-(3,4-dimethoxyphenyl)ethoxy]-4-isopropyl-2,4,6-cycloheptatrien-1-one;

17A) 7-[4-(4,4'-difluorobenzhydryl)piperazino-1-methyl]-2-[3-(dimethylamino)propoxy]-4-isopropyl-2,4,6-cycloheptatrien-1-one;

18A) 7-[4-(4,4'-difluorobenzhydryl)piperazino-1-methyl]-2-[3-(N-methyl-N-phenethylamino)propoxy]-4-isopropyl-2,4,6-cycloheptatrien-1-one;

19A) 7-[4-(4-chlorobenzhydryl)piperazino-1-methyl]-2-methoxy-2,4,6-cycloheptatrien-1-one; and 20A) 7-[4-(4-chlorobenzhydryl)piperazino-1-methyl]-2-methoxy4-phenyl-2,4,6-cycloheptatrien-1-one.

The tropolone derivative of the present invention represented by the general formula (IA) can be produced, for example, according to the following reaction scheme.

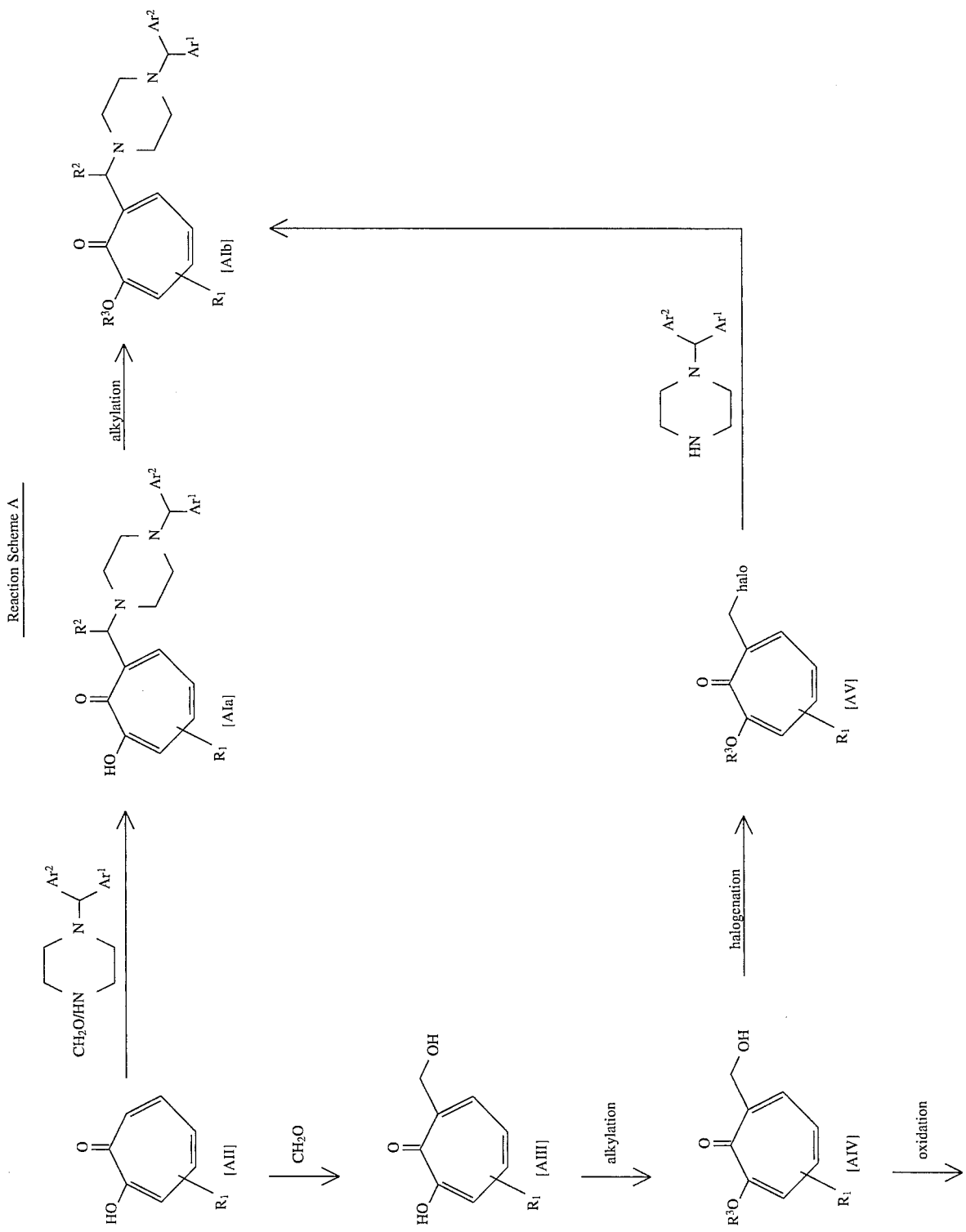

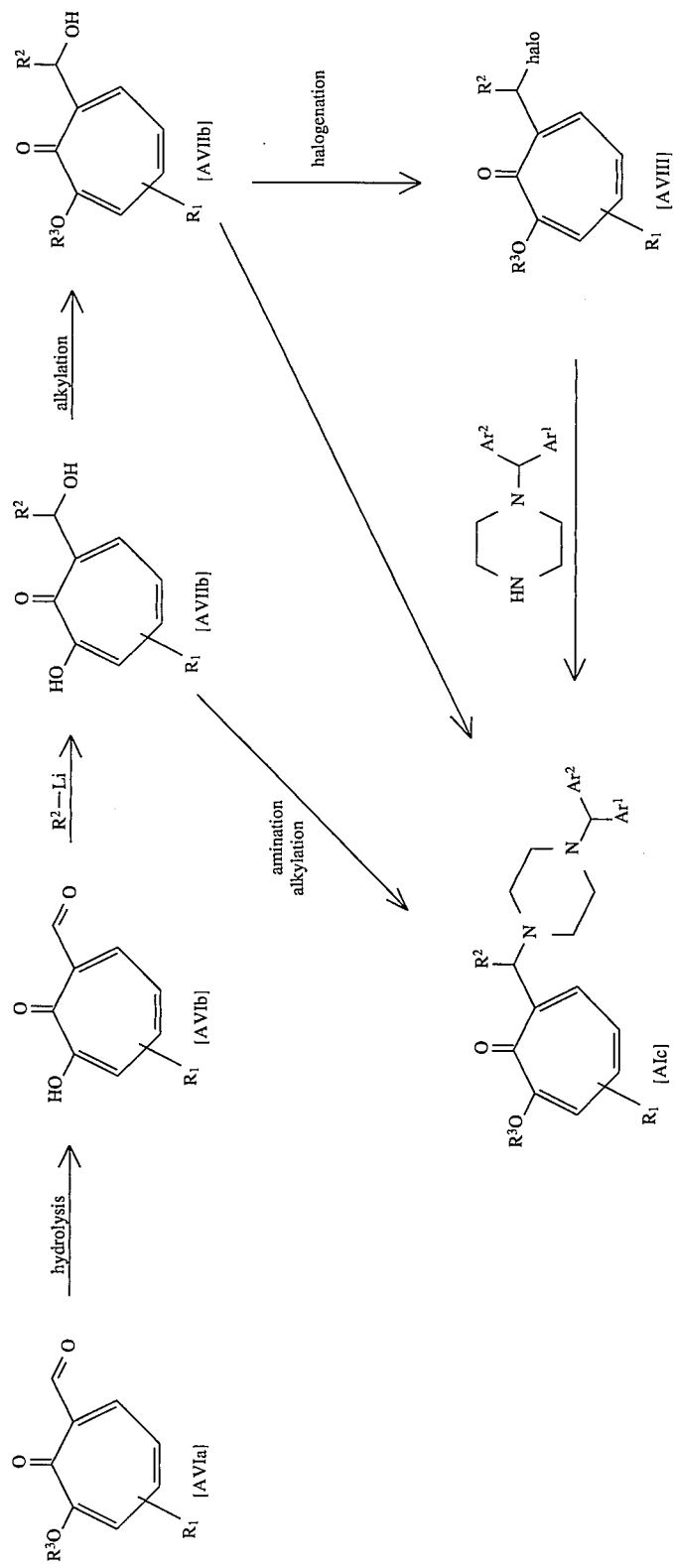

(wherein $R_1$, $R_2$, $R_3$, $Ar_1$ and $Ar_2$ are as defined above, halo is a halogen atom such as chloro, bromo, iodo).

That is, tropolone represented by the general formula [AII] is subjected to an aminomethylation reaction with formaldehyde and a piperazine derivative to synthesize tropolone derivative [AIa]. This reaction is carried out in the presence or absence of inert solvent, for example, acetone, dimethylsulfoxide, dimethylformaldehyde, alcohols such as methanol, ethanol, ethers such as tetrahydrofuran, a solvent containing halogen such as dichloromethane, chloroform, using formaldehyde and a piperazine derivative (1–3 equivalent of the compound [AII], each) and acetic acid (0.5–3 equivalent) by heating at room temperature to 100° C. A particularly preferable process is a process wherein formaldehyde and a piperazine derivative (e.g., 1–1.2 equivalent of the compound [AII]) and acetic acid are heated at room temperature to 65° C. As for the alkylation reaction of tropolone derivative [AIa], the methods which are generally employed for the alkylation reaction of phenols can be employed. For example, as an alkylating agent, alkyl halide or aryl halide such as methyl iodide, benzyl chloride and sulfate esters such as dimethyl sulfate may be used, and as a base, sodium hydride, amine such as triethylamine, an alkali such as sodium hydroxide, potassium hydroxide, potassium carbonate, sodium bicarbonate or the like may be used. The above alkylating agent (1–3 equivalent of the compound [AIa]) and the base (catalytic amount to 5 eq.) are used, which are heated with the compound [AIa] in the aforementioned inert solvent at 0°–100° C. to give tropolone derivative [AIb].

On the other hand, tropolone [AII] is allowed to react with formaldehyde according to a method disclosed in the literature [Proc. Japan Acad.,27, 561 (1951)] to give the compound [AIII] wherein a hydroxymethyl group is introduced into the position 7, then converted to the compound [AIV] by the aforementioned alkylation. The compound [AIV] may be halogenated with amine such as pyridine or triethylamine and methanesulfonyl chloride (1–3 eq.) in the presence or absence of an inert solvent, for example, acetone, dimethylsulfoxide, dimethylformaldehyde, ether such as tetrahydrofuran, a solvent containing halogen such as dichloromethane, chloroform at 0°–100° C. to give the tropolone derivative [AV]. Conversion of the tropolone derivative [AV] to the tropolone derivative [AIb] can be readily conducted by heating at room temperature to 100° C. with piperazine compound (1–3 eq.) and amine such as pyridine, triethylamine, or alkali such as sodium carbonate, sodium bicarbonate in the presence or absence of an inert solvent, for example, acetone, dimethylsulfoxide, demethylformaldehyde, alcohols such as methanol, ethanol, ether such as tetrahydrofuran, a solvent containing halogen such as dichloromethane, chloroform.

The compound [AIc] which is tropolone derivative [AI] having substitutent $R^2$ can be synthesized as follows:

The compound [AIV] is oxidized using manganese dioxide (5–20 equivalent of the compound [AIV]) in a halogenated hydrocarbon solvent such as methylene chloride, chloroform at 0°–50° C., preferably at room temperature to prepare the compound [AVIa]. The compound [AVIa] is hydrolyzed with an aqueous solution or an alcoholic solution of sodium hydroxide, potassium hydroxide or the like (1–5 eq.) at room temperature according to the conventional method to give the compound [AVIb]. The compound [AVIb] can be converted to the compound [AVIIa] wherein a substitutent $R^2$ is introduced by a reaction with organic lithium reagent $R^2$-Li such as methyllithium, n-butyllithium, phenyllithium in a solvent such as tetrahydrofuran in an inert gas atmosphere. The compound [AVIIa] can be converted to the compound [AVIIb] according to the same procedure as that of the aforementioned alkylation. Conversion of the compound [AVIIb] to the tropolone derivative [AIc] can be conducted in one-step by heating with 4-substituted piperazine (1–5 equivalent of the compound [AVIIb]) in an aromatic hydrocarbon solvent such as toluene, xylene. Alternatively, it may be prepared by two-step reaction, that is, it is halogenated in the same manner as described above to give the compound [AVIII], then reacted with 4-substituted piperazine.

Thus obtained compound of the present invention represented by the general formula [IA] can be isolated and purified by the conventional method such as recrystallization, and chromatography.

Additional embodiments of the compounds of the present invention represented by the general formula [IB] are:

1B) 2-(2'-oxo-3'-methoxy-5'-isopropyl-3',5',7'-cycloheptatrienyl)-3-(2-phenethylbenzothiazoline;

2B) 2-(2'-oxo-3'-methoxy-5'-isopropyl-3',5',7'-cycloheptatrienyl)-3-methylbenzothiazoline;

3B) 2-(2'-oxo-3'-methoxy-5'-isopropyl-3',5',7'-cycloheptatrienyl)-3-benzylbenzothiazoline;

4B) 2-(2'-oxo-3'-methoxy-5'-isopropyl-3',5',7'-cycloheptatrienyl)-3-(2-picolyl)benzothiazoline;

5B) 2-(2'-oxo-3'-methoxy-5'-isopropyl-3',5',7'-cycloheptatrienyl)-3-(3-picolyl)benzothiazoline;

6B) 2-(2'-oxo-3'-methoxy-5'-isopropyl-3',5',7'-cycloheptatrienyl)-3-(4-picolyl)benzothiazoline;

7B) 2-(2'-oxo-3'-methoxy-5'-isopropyl-3',5',7'-cycloheptatrienyl)-3-[2-(2-pyridyl)ethyl]benzothiazoline;

8B) 2-(2'-oxo-3'-methoxy-5'-isopropyl-3',5',7'-cycloheptatrienyl)-3-[2-(3,4-dimethoxyphenyl)ethyl]benzothiazoline;

9B) 2-(2'-oxo-3'-methoxy-5'-isopropyl-3',5',7'-cycloheptatrienyl)-3-(2-quinolyl)methylbenzothiazoline;

10B) 2-(2'-oxo-3'-methoxy-5'-isopropyl-3',5',7'-cycloheptatrienyl)-3-[3-(N-methyl-N-phenethylamino)propyl]benzothiazoline;

11B) 2-(2'-oxo-3'-methoxy-5'-isopropyl-3',5',7'-cycloheptatrienyl)-3-[2-(N,N-dimethylamino)ethyl]benzothiazoline;

12B) 2-(2'-oxo-3'-methoxy-5'-isopropyl-3',5',7'-cycloheptatrienyl)-3-[3-(N,N-dimethylamino)propyl]benzothiazoline;

13B) 2-(2'-oxo-3'-methoxy-5'-isopropyl-3',5',7'-cycloheptatrienyl)-3-{3-[4-(4',4'-difluorobenzhydryl)piperazin-1-yl)propyl}benzothiazoline;

14B) 2-(2'-oxo-3'-methoxy-5'-isopropyl-3',5',7'-cycloheptatrienyl)-3-methylbenzothiazoline;

15B) 2-(2'-oxo-3'-(1-piperadinyl)-5'-isopropyl-3',5',7'-cycloheptatrienyl)-3-phenethylbenzothiazoline;

16B) 2-(2'-oxo-3'-(2-(N,N-dimethyl)aminoethyl)amino-5'-isopropyl-3',5',7'-cycloheptatrienyl)-3-(2-phenethylbenzothiazoline;

17B) 2-(2'-oxo-3'-methoxy-5'-isopropyl-3',5',7'-cycloheptatrienyl)-3-(2-phenethyl-1,1-dioxobenzothiazoline; and 18B) 2-(2'-oxo-3'-methoxy-5'-isopropyl-3',5',7'-cycloheptatrienyl)-3-(2-phenethyl-1-oxobenzothiazoline.

The tropolone derivative of the present invention represented by the general formula [IB] can be produced, for example, according to the following reaction scheme:

Reaction Scheme B

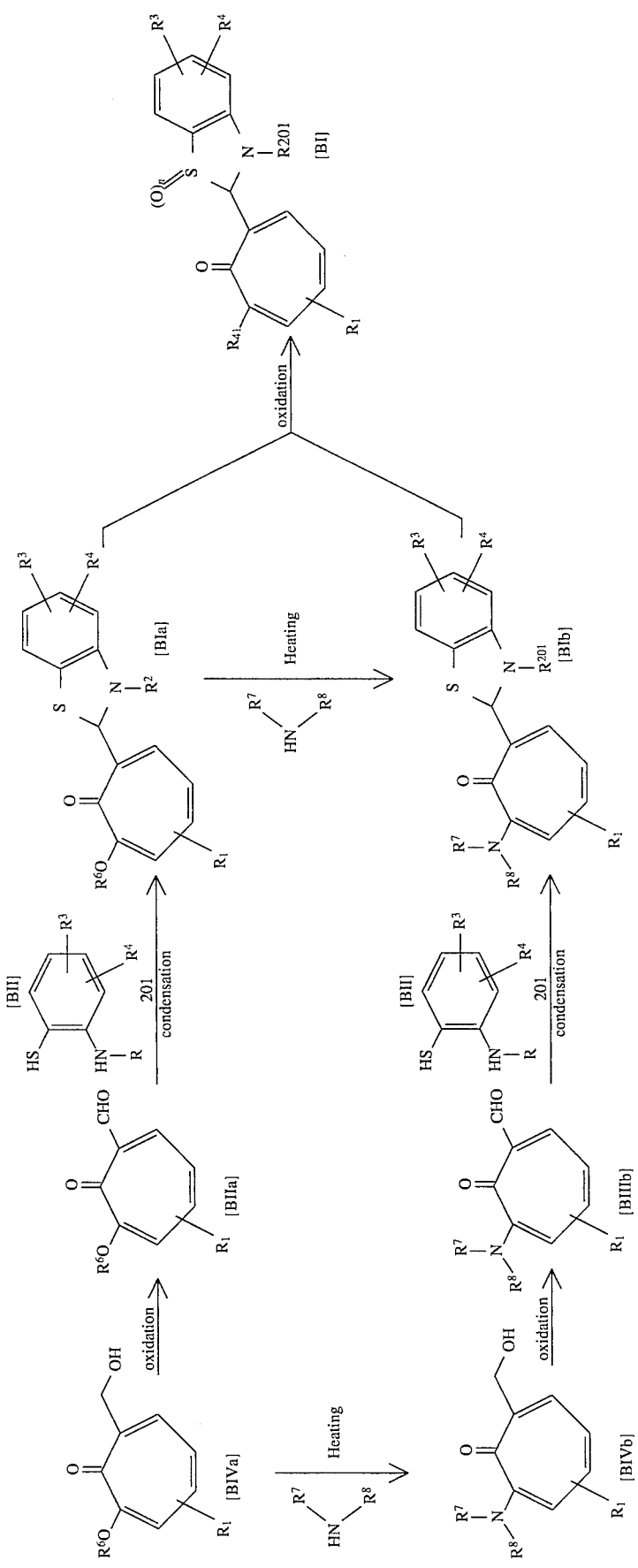

(wherein $R_1$, $R_{201}$, $R_3$, $R_4$, $R_5$, $R_6$, $R_7$, $R_8$, n and $R_{41}$ are as defined above)

That is, a tropolone represented by the general formula [BVI] is allowed to react with formaldehyde according to the method disclosed in the literature [Proc. Japan Acad.,27, 561 (1951)] to give the compound [BV] wherein a hydroxymethyl group is introduced into the position 7, then converted to the compound [BIVa] by the aforementioned alkylation reaction. As the alkylation reaction, the methods which are generally employed for alkylation reaction of phenols can be employed. For example, the reaction can be conducted in the presence of a base using an alkylating agent corresponding to the objective alkyl group such as methyl iodide, benzyl chloride, or sulfate derivatives of the objective alkyl group such as dimethyl sulfate. Examples of the base include sodium hydride, amines such as triethylamine, sodium hydroxide, potassium hydroxide, potassium carbonate, sodium bicarbonate or the like. The above alkylating agent (1–3 equivalent amounts of the compound [BV]) is used. The amount of a base varies according to the kind of reagent, for example, sodium hydride (1–1.2 equivalent amounts) and amines and potassium carbonate (2–5 equivalent amounts) are normally used. The reaction solvent may be any inert solvent, preferably ethers such as tetrahydrofuran, solvents containing halogen such as dichlormethane, chloroform, or polar solvents such as dimethylsulfoxide, dimethylformamide. The reaction temperature varies according to a kind of a base and alkylating agent and, the range between 0°–100° C. is normally preferred.

The compound [BIVa] can be converted to the compound [BIVb] only by heating in the presence of the objective amine and an aromatic hydrocarbon such as benzene, toluene, xylene, or a solvent containing halogen such as carbon tetrachloride, tetrachlorethylene. The amount of amine to be used may be normally 1 to 2 equivalent amounts, particularly 1.2 to 1.5 equivalent amounts based on the compound [BIVa] and they may be used in an excessive amount.

The oxidation reaction of the compounds [BIVa] and [BIVb] can be conducted by using manganese dioxide (5–20 equimolar of the compounds [BIVa] and [BIVb]) at 0°–50° C., preferably at room temperature to convert to the compounds [BIIa] and [BIIb], respectively.

The compounds [BIIIa] and [BIIIb] are condensed with 2-Aminothiophenols to give the compounds [BIa] and [BIb], respectively. The condensation reaction can be conducted using a solvent containing halogen such as dichlormethane, chloroform, an aromatic hydrocarbon such as benzene, toluene, xylene, an aromatic hydrocarbon containing nitrogen such as pyridine quinoline and the like, preferably at room temperature to 100° C. 2-aminothiophenols [BII] may be used in an excessive or small amount based on the compound [BIII], but it is preferred that they are used in almost the same equivalent as that of the compound [BIII] in view of the reaction yield and isolation and purification process of the product. Further, the condensation reaction may be conducted using its oxidized dimer, compound [BII'] instead of the compound [BII] under a reduction condition. That is, those containing an SH group such as the compound [BII] sometimes oxidized by air during storage or during treatment for reaction to convert to the compound [BII']. In that case, the compound [BII'] is retreated with a reducing agent such as sodium borohydride to return to the compound [BII], or the compounds [BIa] and [BIb] can be synthesized by reacting the compound [BIII] and [BII'] in the presence of trivalent phosphorous compound (⅓ to the same moles of the compound [BIII]) such as triethyl phosphate, triphenyl phosphine, tricyclohexyl phosphine and the like. The compound [BIa] can also be converted to the compound [BIb] by reacting with various amines in the aforementioned reaction condition. The compound wherein $R^2$ contains an arylsulfonyl group can be easily synthesized by using the corresponding compound [IB] wherein $R^2$ is H and reacting it with the corresponding arylsulfonyl chloride in the presence of an organic amine such as pyridine, triethylamine.

The obtained compound of the present invention represented by the general formula [IB] can be isolated and purified by conventional method such as recrystallization, column chromatography.

The embodiments of the compound of the present invention represented by the general formula [IC] will be shown below:

1C) 7-[4-(4,4'-difluorobenzhydryl)piperazino-1-methyl]-2-(N-2-dimethylaminoethylamino)-4-isopropyl-2,4,6-cycloheptatrien-1-one;

2C) 7-[4-(4,4'-difluorobenzhydryl)piperazino-1-methyl]-2-(N-3-dimethylaminopropylamino)-4-isopropyl-2,4,6-cycloheptatrien-1-one;

3C) 7-[4-(4,4'-difluorobenzhydryl)piperazino-1-methyl]-4-isopropyl-2-(N-2-methylaminoethylamino)-2,4,6-cycloheptatrien-1-one;

4C) 2-(N-2-aminoethylamino)-7-[4-(4,4'-difluorobenzhydryl)piperazino-1-methyl]-4-isopropyl-2,4,6-cycloheptatrien-1-one;

5C) 7-[4-(4,4'-difluorobenzhydryl)piperazino-1-methyl]-2-(N-2-dimethylaminoethyl-N-methylamino)-4-isopropyl-2,4,6-cycloheptatrien-1-one;

6C) 7-[4-(4,4'-difluorobenzhydryl)piperazino-1-methyl]-2-(N-2-dimethylaminoethyl-N-ethylamino)-4-isopropyl-2,4,6-cycloheptatrien-1-one;

7C) 2-(N-2-diethyaminoethylamino)-7-[4-(4,4'-difluorobenzhydryl)piperazino-1-methyl]-4-isopropyl-2,4,6-cycloheptatrien-1-one;

8C) 2-[N-2-(N'-2-aminoethylamino)ethylamino]-7-[4-(4,4'-difluorobenzhydryl)piperazino-1-methyl]-4-isopropyl-2,4,6-cycloheptatrien-1-one;

9C) 7-[4-(4,4'-difluorobenzhydryl)piperazino-1-methyl]-4-isopropyl-2-[N-2-(2-pyridylamino)ethylamino]-2,4,6-cycloheptatrien-1-one;

10C) 7-[4-(4,4'-difluorobenzhydryl)piperazino-1-methyl]-4-isopropyl-2-[N-2-(2-pyrimidylamino)ethylamino]-2,4,6-cycloheptatrien-1-one;

11C) 7-[4-(4,4'-difluorobenzhydryl)piperazino-1-methyl]-4-isopropyl-2-[(N-2-(2-pyridyl)ethylamino]-2,4,6-cycloheptatrien-1-one;

12C) 7-[4-(4,4'-difluorobenzhydryl)piperazino-1-methyl]-4-isopropyl-2-(N-2-pyridylmethylamino)ethylamino)-2,4,6-cycloheptatrien-1-one;

13C) 7-[4-(4,4'-difluorobenzhydryl)piperazino-1-methyl]-2-(N-2-hydroxyethylamino)-4-isopropyl-2,4,6-cycloheptatrien-1-one;

14C) 7-[4-(4,4'-difluorobenzhydryl)piperazino-1-methyl]-4-isopropyl-2-(N-2-methoxyethylamino)-2,4,6-cycloheptatrien-1-one;

15C) methyl 2-{N-7-[4-(4,4'-difluorobenzhydryl)piperazino-1-methyl]-4-isopropyl-1-oxo-2,4,6-cycloheptatrien-2-ylamino}acetate;

16C) ethyl 3-{N-7-[4-(4,4'-difluorobenzhydryl)piperazino-1-methyl]-4-isopropyl-1-oxo-2,4,6-cycloheptatrien-2-ylamino}propionate;

17C) 7-[4-(4,4'-difluorobenzhydryl)piperazino-1-methyl]-4-isopropyl-2-piperidino-2,4,6-cycloheptatrien-1-one;

18C) 7-[4-(4,4'-difluorobenzhydryl)piperazino-1-methyl]-4-isopropyl-2-morpholino-2,4,6-cycloheptatrien-1-one:

19C) 7-[4-(4,4'-difluorobenzhydryl)piperazino-1-methyl]-4-isopropyl-2-(1-piperazino)-2,4,6-cycloheptatrien-1-one;

20C) 7-[4-(4,4'-difluorobenzhydryl)piperazino-1-methyl]-2-[4-(3-ethylamino-2-pyridyl)pipererazino]-4-isopropyl-2,4,6-cycloheptatrien-1-one;

21C) 7-[4-(4,4'-difluorobenzhydryl)-2,6-dimethylpiperazino-1-methyl]-4-isopropyl-2-methoxy-2,4,6-cycloheptatrien-1-one;

22C) 7-[4-(4,4'-difluorobenzhydryl)-2-methylpiperazino-1-methyl]-4-isopropyl-2-methoxy-2,4,6-cycloheptatrien-1-one;

23C) 7-[4-(4,4'-difluorobenzhydryl)hexahydro-1H-1,4-diazepin-1-ylmethyl]-4-isopropyl-2-methoxy-2,4,6-cycloheptatrien-1-one;

24C) 7-[4-(4,4'-difluorobenzhydryl)-2,6-dimethylpiperazino-1-methyl]-2-(N-2-dimethylaminoethyl-N-methylamino)-4-isopropyl-2,4,6-cycloheptatrien-1-one;

25C) 7-[4-(4,4'-difluorobenzhydryl)-2-methylpiperazino-1-methyl]-2-(N-2-dimethylaminoethyl-N-methylamino)-4-isopropyl-2,4,6-cycloheptatrien-1-one;

26C) 7-[4-(4,4'-difluorobenzhydryl)hexahydro-1H-1,4-diazepin-1-ylmethyl]-2-(N-2-dimethylaminoethyl-N-methylamino)-4-isopropyl-2,4,6-cycloheptatrien-1-one;

27C) 7-[4-(4-chlorobenzhydryl)piperazino-1-methyl]-2-(N-2-dimethylaminoethyl-N-methylamino)-4-isopropyl-2,4,6-cycloheptatrien-1-one;

28C) 7-(4-benzhydrylpiperazino-1-methyl)-2-(N-2-dimethylaminoethyl-N-methylamino)-4-isopropyl-2,4,6-cycloheptatrien-1-one;

29C) 2-(N-2-dimethylaminoethyl-N-methylamino)-4-isopropyl-7-[4-(4-trifluoromethylbenzhydryl)piperazino-1-methyl]-2,4,6-cycloheptatrien-1-one;

30C) 7-[4-(4-chloro-4'-methoxybenzhydryl)piperazino-1-methyl]-2-(N-2-dimethylaminoethyl-N-methylamino)-4-isopropyl-2,4,6-cycloheptatrien-1-one;

31C) 7-[4-(4,4'-difluorobenzhydryl)piperazino-1-methyl]-2-(N-2-dimethylaminoethyl-N-methylamino)-2,4,6-cycloheptatrien-1-one; and 32C) 7-[4-(4,4'-difluorobenzhydryl)piperazino-1-methyl]-2-(N-2-dimethylaminoethyl-N-methylamino)-4-phenyl-2,4,6-cycloheptatrien-1-one.

The tropolone derivative of the present invention represented by the general formula [I] can be produced, for example, according to the following reaction scheme:

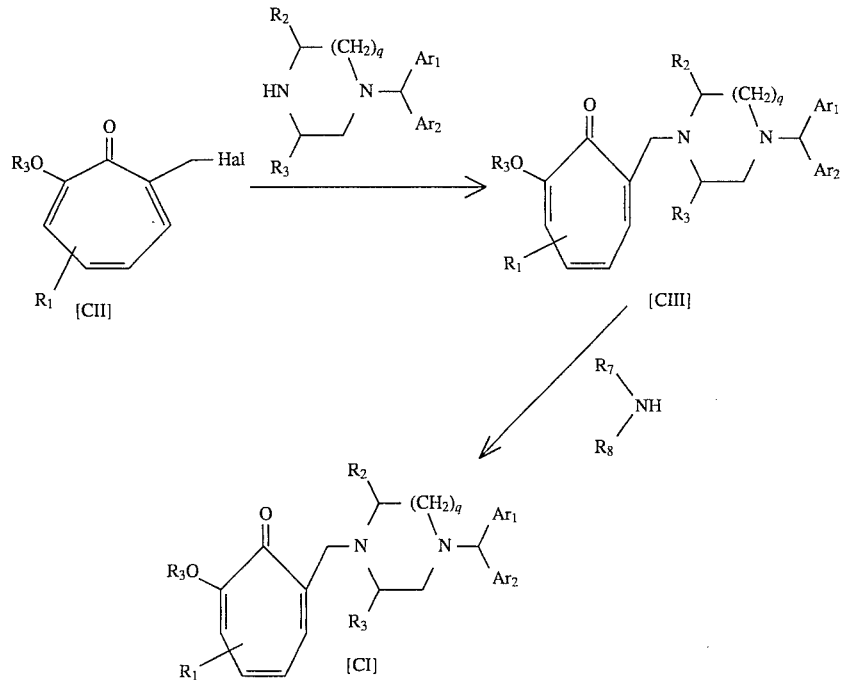

Reaction Scheme C (wherein $R_1$, $R_2$, $R_3$, $R_4$, $Ar_1$, $Ar_2$, are as defined above, and Hal is a halogen atom such as chloro, bromo, iodo)

That is, the compound [CII] is heated with a piperazine compound (1–3 mole equivalent) and amines such as pyridine, triethylamine or alkalis such as sodium hydroxide, cesium carbonate, sodium bicarbonate in the presence or absence of inert solvent, for example, hexamethylphospholictriamide, dimethylsulfoxide, dimethylformamide, acetone, benzene, alcohols such as methanol, ethanol, ethers such as ethyl ether, tetrahydrofuran, a solvent containing halogen such as dichloromethane, chloroform, at room temperature to 100° C. to obtain the compound [CIII]. The conversion of the compound [CIII] into [CI] can easily be conducted in the presence or absence of the aforementioned inert solvent except for alcohols by heating with an amine compound (1–10 equivalent amounts of the compound [CI []) at room temperature to solvent refluxing temperature. If the amine used for the reaction with [CIII] is the salt form such as hydrochloride, the co-use of amines such as pyridine, thriethylamine, diisopropyl amine will be recommended.

The compound can also be produced, for example, according to the processes described above for compounds of the formula IA.

The pharmacological utility of the compounds of the present application is seen by the following tests (both in vitro and in vivo) using the compounds of the present invention and a control agent, and the results are shown.

1. in vitro Anti-lipid peroxidation effect

Protocol A

Brain microsomal fractions were prepared from male rats of SD strain, and a portion (0.2 mg protein) was incubated at 37° C. for 15 minutes with a mixture of $Fe^{3+}$ (0.1 mM)—ADP (0.5 mM) in the presence or absence of the test compound, in final volume of 1 ml of 10 mM HEPES, 150 mM KCl, 0.2 mM NADPH, pH 7.4. After incubation, 1.5 ml of TCA-TBA-HCl reagent (16.7% trichloroacetic acid, 0.4% thiobarbituric acid, 0.278N hydrochloric acid) was added and the reaction mixture was heated in a boiling water for 15 minutes. After cooling in ice-bath, the reaction mixture was centrifuged, and the absorbance of the supernatant at 535 nm was measured. The amount of thiobarbituric acid reactive substance (TBAR) was obtained by calculation using an extinction coefficient of $1.56 \times 10^5 \ M^{-5} \ cm^{-1}$. The test compound was allowed to react at the concentration of 10 μM and 50 μM, and the inhibition ratio of TBAR production at each concentration showed the antiperoxidation activity of the drug. The results are shown in Table 1A for compounds of the formulas IA, IB, and IC, respectively. The compounds with highest inhibition rate have the greatest anti-lipid peroxidation effect.

TABLE 1A

Anti-Lipid Peroxidation Effect

| Compound No. | Anti-Lipid Peroxidation (% inhibition) | |
|---|---|---|
| | 10 μM | 50 μM |
| 1A | 6.7 | <21.3 |
| 2A | 28.8 | 84.7 |
| 3A | 13.8 | 16.3 |
| 4A | 25.8 | 75.1 |
| 5A | 30.5 | 38.7 |
| 6A | 15.9 | 63.2 |
| 7A | 27.2 | 59.2 |
| 8A | 32.3 | 51.8 |
| 9A | 29.2 | 88.1 |
| 10A | 24.0 | 81.6 |
| 12A | 21.4 | 50.4 |
| 13A | 23.1 | 27.4 |
| 15A | 22.4 | 29.0 |
| 16A | 19.1 | 19.1 |
| 18A | 37.0 | 93.1 |

TABLE 1B

Anti-Lipid Peroxidation Effect

| Compound No. | Anti-Lipid Peroxidation (% inhibition) | |
|---|---|---|
| | 10 μM | 50 μM |
| 1B | 91.8 | 93.1 |
| 2B | 95.5 | — |
| 4B | 95.7 | 99.3 |
| 5B | 95.9 | 100 |
| 6B | 93.1 | 96.6 |
| 7B | 91.9 | 94.3 |
| 8B | 93.4 | 93.8 |
| 9B | 94.9 | 96.6 |
| 10B | 93.0 | 94.5 |
| 11B | 89.3 | — |
| 12B | 89.4 | — |
| 13B | 91.8 | 94.4 |
| 14B | 90.0 | — |
| 15B | 93.0 | 94.4 |
| 16B | 91.2 | 95.1 |

TABLE 1C

Anti-Lipid Peroxidation Effect

| Compound No. | Anti-Lipid Peroxidation (% inhibition) | |
|---|---|---|
| | 10 μM | 50 μM |
| 1C | 59.4 | 95.3 |
| 2C | 29.6 | 90.8 |
| 3C | 88.0 | 91.6 |
| 4C | 45.2 | 92.9 |
| 5C | 32.2 | 90.6 |
| 6C | 35.9 | 91.5 |
| 7C | 21.3 | 90.4 |
| 8C | 33.1 | 92.2 |
| 9C | 88.1 | 91.6 |
| 10C | 46.3 | 92.5 |
| 11C | 32.2 | 89.8 |
| 12C | 86.4 | 89.3 |
| 13C | 36.9 | 89.5 |
| 14C | 27.0 | 90.4 |
| 15C | 38.6 | 79.8 |
| 16C | 29.1 | 58.0 |
| 17C | 32.4 | 44.1 |
| 18C | 26.7 | 41.2 |
| 19C | 30.1 | 89.1 |
| 20C | 91.6 | 93.8 |
| 21C | 47.8 | 89.9 |
| 22C | 32.8 | 88.7 |
| 23C | 21.6 | 90.7 |

2. in vitro Ca-antagonism

A strip of pig right coronary artery was depolarized with high $K^+$ (75 mM) for 30 minutes to induce voltage dependent $^{45}Ca$-influx. The extracellular $^{45}Ca$ was chelated by adding EGTA and removed by washing, then the strip was lysed at 100° C. $^{45}Ca$ in this lysate was measured as intracellular $^{45}Ca$ by a scintillation counter. The concentration of the test compound was $10^{-7}$, $10^{-6}$, $10^{-5}M$, and applied until depolarization by $K^+$ was completed. Ratio of inhibition at various concentrations of the test compounds for increasing the intracellular $^{45}Ca$ by $K^+$ was determined. The results are shown in Table 2. The compound with high inhibition ratio has strong Ca-antagonism.

TABLE 2A

Ca-Antagonism

| Compound No. | Ca-Antagonism (% inhibition) (10 μM) |
|---|---|
| 1A | 44 |
| 2A | 61 |
| 3A | 0 |
| 4A | 45 |
| 5A | 19 |
| 6A | 100 |
| 7A | 100 |
| 8A | 27 |
| 9A | 45 |
| 10A | 53 |
| 12A | 72 |
| 13A | 38 |
| 15A | 20 |
| 16A | 52 |

TABLE 2C

Ca-Antagonism

| Compound No. | Ca-Antagonism (% inhibition) (10 μM) |
|---|---|
| 1C | 81 |
| 2C | 63 |
| 3C | 49 |
| 4C | 54 |
| 5C | 94 |
| 6C | 87 |
| 7C | 67 |
| 8C | 60 |
| 9C | 38 |
| 10C | 65 |
| 11C | 62 |
| 12C | 47 |
| 13C | 90 |
| 14C | 71 |
| 15C | 92 |
| 16C | 47 |
| 17C | 53 |
| 18C | 84 |
| 19C | 62 |
| 20C | 30 |
| 21C | 42 |
| 22C | 66 |
| 23C | 86 |

3. in vitro Coronary vasodilation effect

Protocol C

The right portion of a porcine coronary artery was isolated, and cut into 3 mm wide strip which was suspended in a organ bath filled with 20 ml of Krebs—Henseleit solution (37° C.). During the experiment the bath solution was aerated with 95% $O_2$+5% $Co_2$. The change in tension was measured using an isometric transducer. After load tension was stabilized, the preparation was contracted with $PGF_{2\alpha}$ ($10^{-6}$–$3\times1^{-6}$M). After the contract level had stabilized the test compound was cumulatively applied from $10^{-8}$ to $10^{-5}$M. Papaverine ($10^{-4}$M) was used to obtain maximal relaxation at the end of the experiment. The result was expressed as the percentage of papverine-induced relaxation, and the concentration of the test compound which gave 25% relaxation of papaverine-induced relaxation was defined as $ED_{25}$. If $ED_{25}$ was less than $10^{-5}$M, the compound was estimated as "active." The results are shown in Table 3. The compound with low $ED_{25}$ value has great coronary vasodilation effect.

TABLE 3

Coronary Vasodilation

| Compound No. | Coronary Vasodilation ($ED_{25}$ μM) |
|---|---|
| 1A | >10 |
| 2A | 1.8 |
| 7A | 1.9 |

4. in vivo Ischemic heart/reperfusion test

Protocol D

Experiment was carried out using rats anesthetized with pentobarbital under artificial respiration. After the forth rib was excised, heart was exposed by thoracotomy, and the thread was placed under the left coronary artery at it origin. Then, the heart was returned and a thread was passed in a tube. Compounds were applied through tail vein. After 10 minutes, the thread in the tube was pulled to occlude coronary artery. Five minutes after occlusion, the thread was loosened again for reperfusion. Then, ventricular arrhythmia was recorded on electrocardiogram (lead II), by sticking needle electrodes into a right fore-limb and a left hind-limb. Duration time of ventricular tachycardia and occurrence of ventricular fibrillation caused after reperfusion were compared between a group receiving the test compounds and a similarly treated vehicle group. If either of two parameters of the group that received the test compound became less than half of that of the group that received the vehicle, the test compound was estimated as "active". The results are shown in Table 4.

TABLE 4

Ischemic Heart/Reperfusion Test

| Compound No. | Minimal Effective Dose (mg/kg, i.v.) |
|---|---|
| 2A | 0.3# |
| 7A | <5 |
| 10B | <5 |
| 11B | <5 |

5. in vivo Behavior test

Protocol E

Bilateral common carotid arteries of both sides of ICR strain male mice (about 8 weeks old) were occluded for 5 minutes while lightly anesthetized, then blood was reperfuged. The test compounds were intraperitoneally administered 10 minutes before occlusion and within 3 hours after reperfusion. Since a day after reperfusion, behavior disorder was evaluated by spontaneous motor activity of exploratory behavior, traction test and passive avoidance test. That is, spontaneous motor activity was evaluated as follows. Motor activity was measured by tilting cage method for 30 minutes since immediately after a mouse was placed in a measurement cage. If the motor activity was at least more than (average of spontaneous motion of the group received solvent) +2×SD, the compound was evaluated as "active." In traction test, both fore limbs of the mouse were placed on the horizontally stretched wire. If the mouse put its hind limb within 2 seconds, the compound was estimated as "active.". In passive avoidance test, a step-through type apparatus was used, and as acquisition trial of blood reperfusion, electrical shock (about 0.5 mA, 3 seconds) was given to the mice as soon as the whole body of mice entered the black room and on the next day test trial was carried out. The mouse which stayed in a light room for at least 300 seconds was estimated as an active example. In all tests, the test compound which provided at least 50% of active animals was determined as "active." The results are shown in Table 5.

TABLE 5

Mouse Cerebral Ischemia/Reperfusion Test

| Compound No. | Administration Route | Minimal Effective Dose (mg/kg) |
|---|---|---|
| 1A | | >10 |
| 2A | | 3# |
| 7A | | <10 |
| 1B | i.p. | 0.1 |
| 2B | i.p. | 1.0 |
| 6B | i.v. | <1.0 |
| 11B | i.p. | 1.0 |
| 12B | i.p. | 1.0 |

:methanesulfonate

6. Normal cerebral flow stream test

Protocol D B

Experiment was carried out using rats anesthetized with urethane. After a cannulas for blood pressure monitoring and that for drug administration were inserted into femoral artery and vein, respectively. Temporal bone was cut away on a brain stereotaxis apparatus and a probe for measurement of cerebral blood flow was placed on dura mater. The cerebral blood flow was measured using a laser Dopplar blood flow meter. Firstly, a solvent of the test compound was administered intravenously and then three doses of the compound were administered in order of dose every fifteen-minute intervals. When an average of increase in cerebral blood flow due to the test compound minus 2×SE was larger than that of change in cerebral blood flow due to the solvent, the dose was estimated as "active". The compound (1B) was active in the dose of not less than 3 mg/kg i.v.

7. in vivo Anti-anoxia effect

Protocol C C

A group (5 mice) of ICR strain male mice (about 8-week-old) were used. One or two hours after the test compounds were orally administered, a lethal dose (3.0 mg/kg) of KCN was administered into tail vein. A period of time to respiratory arrest and a survival rate were measured. The test compound which provided at least 50% of active example was determined as "active". The results are shown in Table 6.

TABLE 6

| | Anti-anoxia effect |
|---|---|
| Compound No. | Minimal Effective Dose (mg/kg, p.o.) |
| 1C | 100* |

*:methansulfonate

As is obvious from the above pharmacological experiments, the compound of the present invention represented by the general formula [I] is useful as a pharmaceutical composition for preventive and treating cerebrovascular diseases such as cerbral hemorrhage, cerebral infarction, subarachnoid hemorrhage, transient ischemic attacks, cerebral injury, sequelae accompanied with brain surgery, or cardiovascular diseases such as variant angina pectoris, unstable angina, myocardial infarction, arrhythmia caused upon reflowing of coronary blood stream by PTCA/PTCR/CABG and the like.

When it is used as such a composition, the compound represented by the general formula [I] can be combined with pharmaceutically acceptable carrier, vehicle, diluent and formulated into an oral or parenteral dosage form such as powder, granulate, tablet, capsule, injection and the like. The dosage varies depending on the administration route, age, weight of the patient, conditions to be treated or the like. For example, when it is orally administered to an adult patient, the dosage may be 10–50 mg, preferably 10–25 mg a day and it can be administered once or divided into several times a day, although greater or lesser amounts may be used, depending on the criteria described above. Within the preferred dosage range, the compound of the present invention represented by the general formula [I] never shows any toxicity.

EXAMPLES

The present invention will be further explained in detail in the following examples, but it is not construed to be limited to them.

EXAMPLE 1

Production of 7-[4-(4-chlorobenzhydryl)piperazino-1-methyl]-2-hydroxy4-isopropyl-2,4,6-cycloheptatrien-1-one Hinokitiol (500 mg, 3.5 mmol), 1-(4-chlorobenzhydryl)piperazine (1.05 g, 3.66 mmol) and acetic acid (0.21 ml, 3.65 mmol) were dissolved in methanol (1 ml) and heated to 60° C. 37% Formalin (0.27 ml, 3.60 mmol) was added to this solution with stirring and the stirring was further continued for 2 hours. The reaction solution was diluted with dichloromethane, washed with water, then dried over sodium sulfate. Solvent was distilled off under reduced pressure to give a crude product, which was crystallized from methanol to give 1.1 g of 7-[4-(4-chlorobenzhydryl)piperazino-1-methyl]-2-hydroxy-4-isopropyl-2,4,6-cycloheptatrien-1-one as a pale yellow crystal (yield, 78%). Melting point, 69°–71° C. MS m/z 462.2067 (462.2074 calculated as $C_{28}H_{31}ClN_2O_2$) $^1$H NMR (CDCl$_3$) δ(ppm) 1.26 (d, 6H, J=7.0 Hz), 2.43 (m, 4H), 2.57 (m, 4H), 2.88 (qui, 1H, J=7.0 Hz), 3.70 (s, 2H), 4.23 (s, 1H), 6.95 (dd, 1H, J=1.4 and 10.3 Hz), 7.1–7.4 (10H), 7.72 (d, 1H, J=10.3 Hz).

EXAMPLE 2

Production of 7-[4-(4-chlorobenzhydryl)piperazino-1-methyl]-4-isopropyl-2-methoxy-2,4,6-cycloheptatrien-1-one:

Hinokitiol (20 g, 0.12 mol) and potassium hydroxide (8 g, 0.12 mol) were dissolved in water (80 ml), and 37% Formalin (12 ml, 0.16 mmol) was added thereto. The reaction solution was heated at 100° C. for 5 hours while stirring. The reaction solution was neutralized with 6N HCl, then the reaction product was extracted with dichloromethane. The extract was dried over sodium sulfate, then concentrated under reduced pressure. The residue was dissolved in acetone (200 ml), potassium carbonate (34 g, 0.25 mol) and dimethyl sulfate (16 ml, 0.16 mol) were added thereto, and the solution was heated and refluxed for an hour with stirring. The precipitate was removed by filtration, and filtrate was concentrated under reduced pressure. The filtration residue was washed with dichloromethane. The resultant was washed with water and dried over sodium sulfate. The solvent was distilled off under reduced pressure and the residue was purified by silica gel column chromatography [(eluent:hexane/ethyl acetate (1:4)] to give 18.5 g of 7-hydroxymethyl-4-isopropyl-2-methyoxy-2,4,6-cycloheptatrien-1-one as a pale yellow oil (yield, 74%). This oil was solidified when allowed to stand at room temperature.

$^1$H NMR (CDCl$_3$) δ(ppm) 1.29 (d, 6H, 6.9 Hz), 2.89 (qui, 1H, J=6.9 Hz), 3.97 (s, 3H), 4.67 (s, 2H), 6.77 (s, 1H), 6.84 (d, 1H, J=9.2 Hz), 7.44 (d, 1H, J=9.2 Hz).

7-hydroxymethyl-4-isopropyl-2-methoxy-2,4,6-cycloheptatrien-1-one (2.81 g, 13.5 mmol) and pyridine (1.31 ml, 16.2 mmol) were dissolved in dichloromethane (5 ml) and cooled to 0° C. The solution was stirred while methanesulfonyl chloride (1.25 ml, 16.2 mmol) was added thereto. After stirred at 0° C. for 2 hours, the reaction solution was slowly brought back to room temperature. After 2 hours, the reaction solution was diluted with dichloromethane, washed with aqueous saturated sodium bicarbonate, water and 2N HCl, then dried over sodium sulfate. The solvent was distilled off under reduced pressure and the residue was purified by silica gel column chromatography [eluent:hexane/ethyl acetate (1:1)] to give 1.38 g of 7-chloromethyl-4-isopropyl-2-methoxy-2,4,6-cycloheptatrien-1-one (yield: 45%) as a pale yellow oil. This oil was solidified when allowed to stand at room temperature.

MS m/z 226 (M⁺)

¹H NMR (CDCl₃) δ(ppm) 1.29 (d, 6H, 6.8 Hz), 2.89 (qui, 1H, J=6.8 Hz), 4.00 (s, 3H), 4.73 (s, 2H), 6.72 (s, 1H), 6.82 (d, 1H, 9.2 Hz), 7.62 (d, 1H, J=9.2 Hz).

7-chloromethyl-4-isopropyl-2-methoxy-2,4,6-cycloheptatrien-1-one (408 mg, 1.80 mmol), 1-(4-chlorobenzhydryl)piperazine (619 mg, 2.16 mmol), triethylamine (0.3 ml, 2.15 mmol) were dissolved in chloroform (5 ml) and heated and refluxed for 20 hours. The reaction solution was diluted with dichloromethane, washed with water, and dried over sodium sulfate. After solvent was distilled off under reduced pressure, the residue was purified by silica gel column chromatography [eluent:hexane/ethyl acetate (1:1)] to give 703 mg of 7-[4-(4-chlorobenzhydryl)piperazino-1-methyl]-4-isopropyl-2-methoxy-2,4,6-cycloheptatrien-1-one as a pale yellow amorphous powder (yield: 82%).

MS m/z 476 (M⁺)

¹H NMR (CDCl₃) δ(ppm) 1.26 (d, 6H, J=7.3 Hz), 2.43 (m, 4H), 2.57 (m, 4H), 2.85 (qui, 1H, J=7.3 Hz), 3.65 (s, 2H), 3.93 (s, 3H), 4.23 (s, 1H), 6.68 (s, 1H), 6.80 (d, 1H, J=9.2 Hz), 7.1–7.4 (9H), 7.67 (d, 1H, J=9.2 Hz).

EXAMPLE 3

Production of 7-{1-[4-(4-chlorobenzhydryl)piperazinomethyl]-α-phenyl}-4-isopropyl-2-methoxy-2,4,6-cycloheptatrien-1-one 7-hydroxymethyl-4-isopropyl-2-methoxy-2,4,6-cycloheptatrien-1-one (20 g, 96 mmol) was dissolved in chloroform (300 ml), to which was added active manganese dioxide (80 g, 920 mmol) in several portions, and the resultant was stirred at room temperature for 4 hours. The insoluble matter was removed by filtration under reduced pressure, the filtrate was concentrated under reduced pressure and the resulting crude product was recrystallized from toluene to give 12.31 g of 7-formyl-4-isopropyl-2-methoxy-2,4,6-cycloheptatrien-1-one as yellow needle-like crystal (yield: 62%). Melting point of the product was 73°–75° C. 10% aqueous sodium hydroxide (50 ml) was added to the aldehyde (5 g, 24 mmol) and stirred overnight at room temperature. The reaction solution was acidified with 10% dilute hydrochloric acid, then extracted with methylene chloride, washed with water, dried, and solvent was distilled off to give a crude crystal (4.78 g). The crude crystal was recrystallized from ethyl acetate/hexane to give 7-formyl-4-isopropyl-2-hydroxy-2,4,6-cycloheptatrien-1-one as a colorless needle-like crystal (yield: quantitative). This compound showed melting point of 76° C., which is identical to that described in the literature (Sci. Repts. Tohoku Univ., I, 37, 367 (1953)]. The compound (1.94 g, 10 mmol) was dissolved in tetrahydrofuran (20 ml), to which was added dropwise 2M phenyl lithium solution (5.2 ml, ca 10 mmol) in a nitrogen atmosphere while cooling to −78° C. The resultant was stirred for 10 minutes. An aqueous saturated sodium chloride was added to the reaction solution, and the resultant was extracted with methylene chloride, dried and the solvent was distilled off. The residue was purified by silica gel column chromatography to give 1.95 g of 7-(α-hydroxybenzyl)-4-isopropyl-2-methoxy-2,4,6-cycloheptatrien-1-one as brown oil (yield: 71%). The compound (1 g, 3.7 mmol) and 1-(4-chlorobenzhydryl)piperazine (1.27 g, 4.4 mmol) were heated and refluxed in xylene (20 ml) for 2 hours, solvent was distilled off under reduced pressure and the residue was purified by silica gel column chromatography [(ethyl acetate/hexane (1:2)] to give 1.71 g of 7-{1-[4-(4-chlorobenzhydryl)piperazinomethyl]-α-phenyl}-4-isopropyl-2-hydroxyl-2,4,6-cycloheptatrien-1-one (yield: 86%).

MS m/z 538.540 (M⁺)

¹H NMR (CDCl₃) δ(ppm) 1.21 (d, 6H, J=6.7 Hz), 2.42 (bs, 8H), 2.82 (m, 1H), 4.22 (s, 1H), 5.03 (s, 1H), 6.8–8.1 (m, 17H).

The compound (1.5 g, 2.8 mmol) was heated and refluxed with dimethyl sulfate (0.46 g, 3.6 mmol) and potassium carbonate (1.15 g, 8.3 mmol) in acetone (20 ml) for an hour. After water was added to the reaction solution, the resultant was extracted with methylene chloride, washed with water, dried and solvent was distilled off. The resulting residue was purified by silica gel column chromatography (ethyl acetate/hexane (1:3–1:1) to give 0.99 g of 7-{1-[4-(4-chlorobenzhydryl)piperazinomethyl-α-phenyl}-4-isopropyl-2-methoxy-2,4,6-cycloheptatrien-1-one as a pale brown amorphous powder (yield: 64%).

MS m/z 552.554 (M⁺)

¹H NMR (CDCl₃) δ(ppm) 1.22 (d, 6H, J=6.5 Hz), 2.38 (bs, 8H), 2.8 (m, 1H), 3.87 (s, 3H), 4.21 (s, 1H), 5.06 (s, 1H), 6.59 (s, 1H), 6.82 (d, 1H, J=10 Hz), 7.0–7.6 (m, 14H), 7.97 (d, 1H, J=10 Hz).

EXAMPLE 4

Production of 7-{1-[4-(4-chlorobenzhydryl)]piperazinomethyl-α-methyl}-4-isopropyl-2-methoxy-2,4,6-cycloheptatrien-1-one 7-formyl-4-isopropyl-2-hydroxy-2,4,6-cycloheptatrien-1-one (2.00 g, 10 mmol) was dissolved in tetrahydrofuran (20 ml) and cooled to −78° C. in a dry ice/acetone bath. A solution of methyllithium the ether (1.4M, 15 ml) was added dropwise to the solution, then dry ice/acetone bath was removed and stirring was continued until the insolubles were dissolved. An aqueous saturated ammonium chloride was added to the reaction mixture and extracted with methylene chloride. The methylene chloride layer was washed with water, dried over anhydrous sodium sulfate and solvent was distilled off to give 2.18 g of 7-(α-hydroxyethyl)-4-isopropyl-2-hydroxy-2,4,6-cycloheptatrien-1-one as a reddish brown oil (yield: quantitative).

MS m/z 208 (M⁺)

¹H NMR (CDCl₃) δ(ppm) 1.28 (d, 6H, J=6.7 Hz), 1.53 (d, 3H, J=6.2 Hz), 2.92 (m, 1H), 5.17 (q, 1H, J=6.2 Hz), 7.03 (d, 1H, J=10.3 Hz), 7.36 (s, 1H), 7.66 (d, 1H, J=10.3 Hz).

The compound (2.09 g, 10 mmol) was heated and refluxed with 1-(4-chlorobenzhydryl)piperazine) (3.17 g, 11 mmol) in toluene (30 ml) for 1.5 hours. Then, solvent was distilled off under reduced pressure, the residue was dissolved in acetone (50 ml). Potassium carbonate (4.19 g, 30 mmol) and dimethyl sulfate (1.66 g, 13 mmol) were added and the resultant was heated and refluxed. After 2 hours, dimethyl sulfate (0.64 g, 5.1 mmol) and potassium carbonate (2.1 g, 15 mmol) were further added and the resultant was heated and refluxed for 30 minutes. The reaction solution was filtered and the residue obtained after concentration of the filtrate was purified by silica gel column chromatography [ethyl acetate/hexane (1:1)] to give 1.82 g of 7-{1-[4-(4-chlorobenzhydryl)]piperazinomethyl-α-methyl}-4-isopropyl-2-methoxy-2,4,6-cycloheptatrien-1-one as a pale brown oil (yield: 37%).

MS m/z 490.492 (M⁺)

¹H NMR (CDCl₃) δ(ppm) 1.21 (d, 3H, J=6.5 Hz), 1.25 (d, 6H, J=6.5 Hz), 1.27 (s, 3H), 2.3–2.6 (8H), 2.83 (1H, m), 3.92

(s, 3H), 4.07 (m, 1H), 4.18 (s, 1H), 6.66 (s, 1H), 6.79 (d, 1H, J=9.7 Hz), 7.1–7.4 (m, 9H), 7.7 (d, 1H, J=9.7 Hz).

EXAMPLE 5

Production of 7-{1-[4-(4-chlorobenzhydryl)]piperazinomethyl]-α-butyl}-4-isopropyl-2-methoxy-2,4,6-cycloheptatrien-1-one 7-formyl-4-isopropyl-2-hydroxy-2,4,6-cycloheptatrien-1-one (1.95 g, 10 mmol) was dissolved in tetrahydrofuran (30 ml) and the resultant was cooled to −78° C. in a dry ice/acetone bath. A solution of n-butyllithium in hexane (1.6M, 14 ml) was added dropwise to the solution, then, the dry ice/acetone bath was removed and the resultant was stirred until insoluble matter was dissolved. An aqueous saturated ammonium chloride was added to the reaction mixture and the resultant was extracted with methylene chloride. The methylene chloride layer was washed with water, then dried over anhydrous sodium sulfate. Solvent was distilled off to give 2.72 g of 7-(α-hydroxybutyl)-4-isopropyl-2-hydroxy-2,4,6-cycloheptatrien-1-one as a reddish brown oil (yield: quantitative).

The compound (2.4 g, 9 mmol) and 1-(4-chlorobenzhydryl)piperazine (2.6 g, 10 mmol) were heated and refluxed in toluene (30 ml) for 2 hours, then solvent was distilled off under reduced pressure and the residue was dissolved in acetone (50 ml), to which were added potassium carbonate (4.23 g, 31 mmol) and dimethyl sulfate (1.93 g, 15 mmol), and the resultant was heated and refluxed for 1.5 hours. The reaction solution was filtered and the residue obtained by concentration of the filtrate was purified by silica gel column chromatography (ethyl acetate/hexane, 1:2–1:1 ) to give 1.55 g of 7-{1-[4-(4-chlorobenzhydryl)piperazinomethyl]-α-butyl}-4-isopropyl-2-methoxy-2,4,6-cycloheptatrien-1-one as a pale brown oil (yield: 32%).

MS m/z 532.534 (M$^+$)

$^1$H NMR (CDCl$_3$) δ(ppm) 0.788 (t, 3H, J=6.8 Hz), 1.0–1.8 (m, 6H), 1.27 (d, 6H, J=6.7 Hz), 2.1–2.7 (8H), 2.84 (m, 1H), 3.92 (s, 3H), 4.16 (s, 1H), 4.22 (m, 1H), 6.66 (s, 1H), 6.78 (d, 1H, J=10 Hz), 7.1–7.4 (m, 9H), 7.51 (d, 1H, J=10 Hz).

EXAMPLE 6

Production of 7-(4-benzhydrylpiperazino-1-methyl)-4-isopropyl-2-methoxy-2,4,6-cycloheptatrien-1-one 7-hydroxymethyl-4-isopropyl-2-methoxy-2,4,6-cycloheptatrien-1-one (400 mg, 1.92 mmol) was dissolved in chloroform (25 ml), to which were added triethylamine (291 mg, 2.88 mmol) and methanesulfonyl chloride (263 mg, 2.30 mmol) and the resultant was stirred at room temperature for 14 hours. The reaction solution was washed with water, the organic layer was dried over anhydrous sodium sulfate and concentrated under reduced pressure. The resulting residue was dissolved in chloroform (30 ml), to which were added triethylamine (291 mg, 2.88 mmol) and 4-benzhydrylpiperazine (485 mg, 1.92 mmol) and the resultant was stirred at 60° C. for 14 hours. The reaction solution was washed with water, and the organic layer was dried over anhydrous sodium sulfate and concentrated under reduced pressure. The resulting residue was purified by silica gel column chromatography and 417 mg of 7-(4-benzhydrylpiperazino-1-methyl)-4-isopropyl-2-methoxy-2,4,6-cycloheptatrien-1-one was obtained as a yellowish brown amorphous powder from the hexane/ethyl acetate (1:1)-eluted fraction (yield: 49%).

MS m/z 442 (M$^+$)

$^1$H NMR (CDCl$_3$) δ(ppm) 1.26 (d, 6H, J=6.8 Hz), 2.4–2.6 (8H), 2.83 (qui, 1H, J=6.8 Hz), 3.64 (s, 2H), 3.93 (s, 3H), 4.24 (s, 1H), 6.68 (s, 1H), 6.80 (d, 1H, J=9.8 Hz), 7.1–7.5 (10H), 7.66 (d, 1H, J=9.8 Hz).

EXAMPLE 7

Production of 7-[4-(4,4'-difluorobenzhydryl)piperazino-1-methyl]-4-isopropyl-2-methoxy-2,4,6-cycloheptatrien-1-one 7-chloromethyl-4-isopropyl-2-methoxy -4-isopropyl-2,4,6-cycloheptatrien-1-one (500 mg, 2.21 mmol), 1-(4,4'-difluorobenzhydryl)piperazine (820 mg, 2.84 mmol) and triethylamine (0.4 ml, 2.87 mmol) were dissolved in chloroform (5 ml), and heated and refluxed for 20 hours. The reaction solution was diluted with dichloromethane, washed with water and dried over sodium sulfate. After solvent was distilled off under reduced pressure, the residue was purified by silica gel column chromatography [eluent:hexane/ethyl acetate (3:7)] to give 808 mg of 7-[4-(4,4'-(difluorobenzhydryl)piperazino-1-methyl]-4-isopropyl-2-methoxy-2,4,6-cycloheptatrien-1-one (yield: 76%) as a pale yellow amorphous powder.

MS m/z 478 (M$^+$)

$^1$H NMR (CDCl$_3$) δ(ppm) 1.26 (d, 6H, J=6.8 Hz), 2.41 (m, 4H), 2.57 (m, 4H), 2.85 (qui, 1H, J=6.8 Hz), 3.66 (s, 2H), 3.93 (s, 3H), 4.23 (s, 1H), 6.69 (s, 1H), 6.80 (d, 1H, J=9.2 Hz), 6.96 (t, 4H, J=8.9 Hz), 7.34 (dd, 4H, J=8.9, 5.4 Hz), 7.66 (d, 1H, J=9.2 Hz).

EXAMPLE 8

Production of 7-{4-[4,4'-di(trifluoromethyl)benzhydryl]piperazino-1-methyl}-4-isopropyl-2-methoxy-2,4,6-cycloheptatrien-1-one 7-hydroxymethyl-4-isopropyl-2-methoxy-2,4,6-cycloheptatrien-1-one (423 mg, 2.03 mmol) was dissolved in chloroform (25 ml), to which were added triethylamine (284 mg, 2.81 mmol) and methanesulfonyl chloride (268 mg, 2.34 mmol), and the resultant was stirred at room temperature for 13 hours. The reaction solution was washed with water, the organic layer was dried over anhydrous sodium sulfate and concentrated under reduced pressure. The resulting residue was dissolved in chloroform (30 ml) to which were added triethylamine (237 mg, 2.34 mmol) and 4-[4,4'-di(trifluoromethyl)benzhydryl]piperazine (500 mg, 1.56 mmol), and the resultant was heated and refluxed for 4 hours. The reaction solution was washed with water, the organic layer was dried over anhydrous sodium sulfate and concentrated under reduced pressure. The resulting residue was purified by silica gel column chromatography [eluent:hexane/ethyl acetate (1:1)] to give 520 mg of 7-{4-[4,4'-di(trifluoromethyl)benzhydryl]piperazino-1-methyl}-4-isopropyl-2-methoxy-2,4,6-cycloheptatrien-1-one as a yellow amorphous powder (yield: 65%).

MS m/z 578 (M$^+$)

$^1$H NMR (CDCl$_3$) δ(ppm) 1.27 (d, 6H, J=6.8 Hz), 2.4–2.6 (8H), 2.85 (qui, 1H, J=6.8 Hz), 3.65 (s, 2H), 3.94 (s, 3H), 4.39 (s, 1H), 6.69 (s, 1H), 6.80 (d, 3H, J=9.6 Hz), 7.6 (6H), 7.65 (d, 1H, J=9.6 Hz).

EXAMPLE 9

Production of 4-isopropyl-2-methoxy-7-[4-(4-trifluoromethylbenzhydryl)piperazino-1-methyl]-2,4,6-cycloheptatrien-1-one 7-hydroxymethyl 4-isopropyl-2-methoxy-2,4,6-cycloheptatrien-1-one (234 mg, 1.12 mmol) was dissolved in chloroform (15 ml), to which were added triethylamine (171 mg, 1.69 mmol) and methanesulfonyl chloride (161 mg, 1.41 mmol), and the resultant was stirred at room temperature for 11 hours. The reaction solution was washed with water, the organic layer was dried over anhydrous sodium sulfate and concentrated under reduced pressure. The resulting residue was dissolved in chloroform (20 ml), to which were added triethylamine (142 mg, 1.41 mmol) and 4-(4-trifluoromethylbenzhydryl)piperazine (364 mg, 0.94 mmol) and the resultant was stirred at 60° C. for 14 hours. The reaction solution was washed with water, the organic layer was dried over anhydrous sodium sulfate and concentrated under reduced pressure. The resulting residue was purified by silica gel column chromatography to give 272 mg of 4-isopropyl-2-methoxy-7-[4-(4-trifluoromethylbenzhydryl)piperazino-1-methyl]-2,4,6-cycloheptatrien-1-one as a yellow amorphous powder from hexane/ethyl acetate (1:1)-eluted fraction (yield: 50%).

MS m/z 510 (M$^+$)

$^1$H NMR (CDCl$_3$) δ(ppm) 1.26 (d, 6H, J=6.8 Hz), 2.4–2.6 (8H), 2.85 (qui, 1H, J=6.8 Hz), 3.64 (s, 2H), 3.93 (s, 3H), 4.31 (s, 1H), 6.68 (s, 1H), 6.80 (d, 1H, J=9.2 Hz), 7.2–7.4 (5H), 7.45–7.60 (4H), 7.66 (d, 1H, J=9.2 Hz).

EXAMPLE 10

Production of 7-[4-(4-chloro-4'-methoxybenzhydryl)piperazino-1-methyl]-4-isopropyl-2-methoxy-2,4,6-cycloheptatrien-1-one 7-hydroxymethyl -4-isopropyl-2-methoxy-2,4,6-cycloheptatrien-1-one (480 mg, 2.30 mmol) was dissolved in chloroform (20 ml), to which were added triethylamine (350 mg, 3.45 mmol) and methanesulfonyl chloride (330 mg, 2.88 mmol), and the resultant was stirred at room temperature for 11 hours. The reaction solution was washed with water, the organic layer was dried over anhydrous sodium sulfate and concentrated under reduced pressure. The resulting residue was dissolved in chloroform (30 ml), to which were added triethylamine (291 mg, 2.88 mmol) and 4-(4-chloro4'-methoxybenzhydryl)piperazine (608 mg, 1.92 mmol), and the resultant was heated and refluxed for 7 hours. The reaction solution was washed with water, the organic layer was dried over anhydrous sodium sulfate and concentrated under reduced pressure. The resulting residue was purified by silica gel column chromatography to give 482 mg of 7-[4-(4-chloro-4'-methoxybenzhydryl)piperazino-1-methyl]-4-isopropyl-2-methoxy-2,4,6-cycloheptatrien-1-one as a pale yellow amorphous powder from the hexane/ethyl acetate (1:1)-eluted fraction (yield: 49%).

MS m/z 510 (M$^+$)

$^1$H NMR (CDCl$_3$) δ(ppm) 1.26 (d, 6H, J=6.8 Hz), 2.4–2.6 (8H), 2.85 (qui, 1H, J=6.8 Hz), 3.64 (s, 2H), 3.93 (s, 3H), 4.31 (s, 1H), 6.68 (s, 1H), 6.80 (d, 1H, J=9.2 Hz), 7.2–7.4 (5H), 7.45–7.60 (4H), 7.66 (d, 1H, J=9.2 Hz).

EXAMPLE 11

Production of 7-[4-(4,4'-difluorobenzhydryl)piperazino-1-methyl]-2-ethoxy-4-isopropyl-2,4,6-cycloheptatrien-1-one 60% oily sodium hydride (256 mg, 6.4 mmol) was added to a solution of 2-hydroxy-7-hydroxymethyl-4-isopropyl-2,4,6-cycloheptatrien-1-one (1.13 g, 5.82 mmol) in dimethylformamide (5 ml) with stirring. Then, ethyl iodide (0.7 ml, 8.75 mmol) was added and the reaction mixture was heated at 70° C. for 3 hours. The reaction solution was diluted with dichloromethane, washed with water, and dried over sodium sulfate. After the solvent was distilled off under reduced pressure, the residue was purified by silica gel column chromatography [eluent:hexane/ethyl acetate (2:3)] to give 485 mg of 2-ethoxy-7-hydroxymethyl 4-isopropyl-2,4,6-cycloheptatrien-1-one as a pale yellow amorphous powder (yield: 76%).

$^1$H NMR (CDCl$_3$) δ(ppm) 1.26 (d, 6H, J=6.8 Hz), 1.55 (t, 3H, J=6.8 Hz), 2.87 (qui, 2H, J=6.8 Hz), 4.16 (q, 2H, J=6.8 Hz), 4.66 (s, 2H), 6.80 (s, 1H), 6.85 (d, 1H, J=9.2 Hz), 7.46 (d, 1H, J=9.2 Hz).

2-ethoxy-7-hydroxymethyl-4-isopropyl-2,4,6-cycloheptatrien-1-one (485 mg, 2.18 mmol) and triethylamine (0.36 ml, 2.58 mmol) were dissolved in dichloromethane (2 ml) and cooled to 0° C. Methanesulfonyl chloride (0.2 ml, 2.58 mmol) was added to the solution with stirring, and stirring was continued for another one hour at 0° C. Then, the reaction solution was slowly warmed to room temperature. After 4 hours, the reaction solution was diluted with dichloromethane, washed with an aqueous saturated sodium bicarbonate and dried over sodium sulfate. After solvent was distilled off under reduced pressure, 1-(4-4'-difluorobenzhydryl)piperazine (756 mg, 2.62 mmol) and triethylamine (0.36 ml, 2.58 mmol) were added to the residue, and the resultant was dissolved in chloroform (15 ml). The reaction solution was heated and refluxed for 7 hours, diluted with dichloromethane, washed with water and dried over sodium sulfate. After solvent was distilled off under reduced pressure, the residue was purified by silica gel column chromatography [eluent:hexane/ethyl acetate (3:7)] to give 638 mg of 7-[4-(4,4'-difluorobenzhydryl)piperazino-1-methyl]-2-ethoxy-4-isopropyl-2,4,6-cycloheptatrien-1-one as a pale yellow amorphous powder (yield: 59%).

MS m/z 492 (M$^+$)

$^1$H NMR (CDCl$_3$) δ(ppm) 1.25 (d, 6H, J=7.0 Hz), 1.52 (t, 3H, J=7.0 Hz), 2.40 (m, 4H), 2.55 (m, 4H), 2.82 (qui, 1H, J=7.0 Hz), 3.62 (s, 2H), 4.12 (1, 2H, J=7.0 Hz), 4.23 (s, 1H), 6.70 (s, 1H), 6.78 (d, 1H, J=9.2 Hz), 6.70 (t, 4H, J=8.9 Hz), 7.34 (dd, 4H, J=8.9, 5.4 Hz), 7.63 (d, 1H, J=9.2 Hz).

EXAMPLE 12

Production of 2-butoxy-7-[4-(4,4'-difluorobenzhydryl)piperazino-1-methyl]-4-isopropyl-2,4,6-cycloheptatrien-1-one A solution of 2-hydroxy-7-hydroxymethyl-4-isopropyl-2,4,6-cycloheptatrien-1-one (1.26 g, 6.49 mmol) in dimethylformamide (5 ml) was stirred, and 60% oily sodium hydride (285 mg, 7.13 mmol) was added in small portions to the solution. Subsequently, butyl iodide (1.1 ml, 9.6 mmol) was added and the reaction solution was heated at 80° C. for 4 hours. The solution was diluted with dichloromethane, washed with water and dried over sodium sulfate. Solvent was distilled off under reduced pressure and the residue was purified by silica gel column chromatography [eluent:hexane/ethyl acetate (1:1)] to give 612 mg of 2-butoxy-7-hydroxymethyl-4-isopropyl-2,4,6-cycloheptatrien-1-one as a yellowish brown oil (yield, 38%).

$^1$H NMR (CDCl$_3$) δ(ppm) 1.00 (t, 3H, J=7.3 Hz), 1.27 (d, 6H, J=6.8 Hz), 1.55 (m, 2H), 1.92 (m, 2H), 2.89 (qui, 1H, J=6.8 Hz), 4.07 (t, 2H, J=7.0 Hz), 4.65 (d, 2H, J=5.4 Hz), 6.79 (s, 1H), 6.81 (d, 1H, J=9.2 Hz), 7.4 (d, 1H, J=9.2 Hz).

2-butoxy-7-hydroxymethyl-4-isopropyl-2,4,6-cycloheptatrien-1-one (6 12 mg, 2.44 mmol) and triethylamine (0.41 ml, 2.94 mmol) were dissolved in dichloromethane (2 ml), and cooled to 0° C. The solution was stirred, while methanesulfonyl chloride (0.23 ml, 2.97 mmol) was added thereto. Stirring was further continued at 0° C. for an hour, then the reaction solution was gradually warmed to room temperature. After 4 hours, the solution was diluted with dichloromethane and washed with aqueous saturated sodium bicarbonate and dried over sodium sulfate. After solvent was distilled off under reduced pressure, 1-(4,4'-difluorobenzhydryl)piperazine (846 mg, 2.93 mmol) and triethylamine (0.41 ml, 2.94 mmol) were added to the residue, which was dissolved in chloroform (15 ml). After heated and refluxed for 12 hours, the solution was diluted with dichloromethane, washed with water and dried over sodium sulfate. After solvent was distilled off under reduced pressure, the residue was purified by silica gel column chromatography [eluent:hexane/ethyl acetate (7:3)] and 823 mg of 2-butoxy-7-[4-(4,4'-difluorobenzhydryl)piperazino-1-methyl]-4-isopropyl-2,4,6-cycloheptatrien-1-one was obtained as a pale yellow amorphous powder was obtained (yield: 64%).

MS m/z 520 (M⁺)

¹H NMR (CDCl₃) δ(ppm) 0.98 (t, 3H, J=7.3 Hz), 1.25 (d, 6H, J=7.0 Hz), 1.53 (m, 2H), 1.89 (m, 2H), 2.40 (m, 4H), 2.55 (m, 4H), 2.82 (qui, 1H, J=7.0 Hz), 3.62 (s, 2H), 4.03 (t, 2H), J=6.8 Hz), 4.23 (s, 1H), 6.70 (s, 1H), 6.77 (d, 1H, J=9.2 Hz), 6.96 (t, 4H, J=8.9 Hz), 7.34 (dd, 4H, J=8.9, 5.4 Hz), 7.62 (d, 1H, J=9.2 Hz).

EXAMPLE 13

Production of 2-benzyloxy-7-[4-(4,4'-difluorobenzhydryl)piperazino-1-methyl]-4-isopropyl-2,4,6-cycloheptatrien-1-one A solution of 2-hydroxy-7-hydroxymethyl-4-isopropyl-2,4,6-cycloheptatrien-1-one (1.15 g, 5.92 mmol) in dimethylformamide (5 ml) was stirred while 60% oily sodium hydride (260 mg, 6.50 mmol) was gradually added thereto. Subsequently, benzyl chloride (1 ml, 8.41 mmol) was added, then the reaction solution was heated at 80° C. for 4 hours. The reaction solution was diluted with dichloromethane, washed with water and dried over sodium sulfate. After solvent was distilled off under reduced pressure, the residue was purified by silica gel column chromatography [eluent:hexane/ethyl acetate (1:1)] to give 729 mg of 2-benzyloxy-7-hydroxymethyl-4-isopropyl-2,4,6-cycloheptatrien-1-one (yield: 43%) as a pale yellowish brown oil.

¹H NMR (CDCl₃) δ(ppm) 1.12 (d, 6H, J=6.8 Hz), 2.77 (qui, 1H, J=6.8 Hz), 4.67 (d, 1H, J=5.9 Hz), 5.29 (s, 2H), 6.80 (d, 1H, J=9.4 Hz), 6.83 (s, 1H), 7.3–7.5 (6H).

2-benzyloxy-7-hydroxymethyl-4-isopropyl-2,4,6-cycloheptatrien-1-one (729 mg, 2.56 mmol) and triethylamine (0.43 ml, 3.09 mmol) were dissolved in dichloromethane (2 ml), and cooled to 0° C. Methanesulfonyl chloride (0.24 ml, 3.1 mmol) was added to the solution with stirring. Further, stirring was continued at 0° C. for an hour, then the reaction solution was gradually warmed to room temperature. After 4 hours, the solution was diluted with dichloromethane, washed with aqueous saturated sodium bicarbonate and dried over sodium sulfate. After solvent was distilled off under reduced pressure, 1-(4,4'-difluorobenzhydryl)piperazine (887 mg, 3.08 mmol) and triethylamine (0.43 ml, 3.09 mmol) were added to the residue, which was dissolved in chloroform (15 ml). The solution was heated and refluxed for 6 hours, then diluted with dichloromethane, washed with water and dried over sodium sulfate. After solvent was distilled off under reduced pressure, the residue was purified by silica gel column chromatography [eluent:hexane/ethyl acetate (7:3)] to give 776 mg of 2-benzyloxy-7-[4-(4,4'-difluorobenzhydryl)piperazino-1-methyl]-4-isopropyl-2,4,6-cycloheptatrien-1-one as a pale yellow amorphous powder (yield: 55%).

MS m/z 554 (M⁺)

¹H NMR (CDCl₃) δ(ppm) 1.11 (d, 6H, J=6.8 Hz), 2.41 (m, 4H), 2.56 (m, 4H), 2.73 (qui, 1H, J=6.8 Hz), 3.64 (s, 2H), 4.23 (s, 1H), 5.24 (s, 2H), 6.76 (s, 1H), 6.77 (d, 1H, J=9.4 Hz), 6.96 (t, 4H, J=8.9 Hz), 7.34 (dd, 4H, J=8.9, 5.4 Hz), 7.2–7.5 (5H), 7.62 (d, 1H, J=9.4 Hz).

EXAMPLE 14

Production of 7-[4-(4,4'-difluorobenzhydryl)piperazino-1-methyl]-2-[2-(3,4-dimethoxyphenyl)ethoxy]-4-isopropyl-2,4,6-cycloheptatrien-1-one A solution of 2-hydroxy-7-hydroxymethyl-4-isopropyl-2,4,6-cycloheptatrien-1-one (844 mg, 4.35 mmol) in dimethylformamide (5 ml) was stirred while 60% oily sodium hydride (191 mg, 4.78 mg) in small portions were added thereto. Subsequently, 3,4-dimethoxyphenethyl iodide (2.54 mg, 8.70 mmol) was added, then the solution was heated at 80° C. for 7 hours. The solution was diluted with dichloromethane, washed with water and dried over sodium sulfate. After solvent was distilled off under reduced pressure, the residue was purified by silica gel column chromatography [eluent:hexane/ethyl acetate (3:2)] to give 169 mg of 2-[2-(3,4-dimethoxyphenyl)ethoxy]-7-hydroxymethyl-4-isopropyl-2,4,6-cycloheptatrien-1-one as a yellowish brown oil (yield: 11%).

¹H NMR (CDCl₃) δ(ppm) 1.24 (d, 6H, J=6.8 Hz), 2.80 (qui, 1H, J=6.8 Hz), 3.19 (t, 2H, J=6.8 Hz), 3.86 (s, 3H), 3.91 (s, 3H), 4.22 (t, 2H, J=6.8 Hz), 4.66 (s, 2H), 6.75 (s, 1H), 6.8–7.0 (4H), 7.43 (d, 1H, J=9.2 Hz).

2-[2-(3,4-dimethoxyphenyl)ethoxy]-7-hydroxymethyl-4-isopropyl-2,4,6-cycloheptatrien-1-one (169 mg, 0.472 mmol) and triethylamine (0.08 ml, 0.574 mmol) were dissolved in dichloromethane (1 ml), to which was added methanesulfonyl chloride (44 µl, 0.568 mmol) at room temperature. After the solution was stirred at room temperature for 5 hours, solvent was distilled off under reduced pressure. 1-(4,4'-difluorobenzhydryl)piperazine (164 mg, 0.569 mmol) and triethylamine (0.08 ml, 0.574 mmol) were added to the residue, which were dissolved in chloroform (5 ml). The solution was heated and refluxed for 12 hours, then diluted with dichloromethane, washed with water and dried over sodium sulfate. After solvent was distilled off under reduced pressure, the residue was purified by silica gel column chromatography [eluent:hexane/ethyl acetate (1:1)] to give 157 mg of 7-[4-(4,4'-difluorobenzhydryl)piperazino-1-methyl]-2-[2-(3,4-dimethoxyphenyl]ethoxy}-4-isopropyl-2,4,6-cycloheptatrien-1-one as a yellowish brown oil (yield: 53%).

MS m/z 628 (M⁺)

¹H NMR (CDCl₃) δ(ppm) 1.21 (d, 6H, J=7.0 Hz), 2.41 (m, 4H), 2.55 (m, 4H), 2.78 (qui, 1H, J=7.0 Hz), 3.17 (t, 2H, J=7.0 Hz), 3.62 (s, 2H), 3.86 (s, 3H), 3.90 (s, 3H), 4.18 (t, 2H, J=7.0 Hz), 4.23 (s, 1H), 6.66 (s, 1H), 6.7–6.9 (4H), 6.96 (t, 4H, J=8.9 Hz), 7.34 (dd, 4H, J=8.9, 5.4 Hz), 7.63 (d, 1H, J=9.2 Hz).

EXAMPLE 15

Production of 7-[4-(4,4'-difluorobenzhydryl)piperazino-1-methyl]-4-isopropyl-2-[3-(N-methyl-N-phenethylamino)propoxy]-2,4,6-cycloheptatrien-1-one 60% oily sodium hydride (292, mg, 7.3 mmol) in small portions were added to a solution of 2-hydroxy-7-hydroxymethyl-4-isopropyl-2,4,6-cycloheptatrien-1-one (1.29 g, 6.64 mmol) in dimethylformamide (5 ml) with stirring. After addition of 1,3-dibromopropane (1.35 ml, 13.3 mmol), the solution was heated at 80° C. for 4 hours. The solution was diluted with dichloromethane, washed with water, and dried over sodium sulfate. After solvent was distilled off under reduced pressure, the residue was purified by silica gel column chromatography [eluent:hexane/ethyl acetate (1:1)] to give 293 mg of 2-(3-bromopropoxy)-7-hydroxymethyl-4-isopropyl-2,4,6-cycloheptatrien-1-one as a pale yellow crystal (yield: 14%).

$^1$H NMR (CDCl$_3$) δ(ppm) 1.29 (d, 6H, J=7.0 Hz), 2.46 (qui, 2H, J=5.9 Hz), 2.8 (qui, 1H, J=7.0 Hz), 3.69 (t, 2H, J=5.9 Hz), 4.22 (t, 2H, J=5.9 Hz), 4.66 (s, 2H), 6.84 (s, 1H), 6.85 (d, 1H, J=9.4 Hz), 7.44 (d, 1H, J=9.4 Hz).

2-(3-bromopropoxy-7-hydroxymethyl-4-isopropyl-2,4,6-cycloheptatrien-1-one (280 mg, 0.89 mmol), N-phenethylamine (0.15 ml, 1.03 mmol), triethylamine (0.15 ml, 1.08 mmol) were dissolved in chloroform (5 ml), and the solution was heated and refluxed for 5 hours. The solution was diluted with dichloromethane, washed with water and dried over sodium sulfate. After solvent was distilled off under reduced pressure, the residue was purified by silica gel column chromatography [eluent:chloroform/methanol (10:1)] to give 242 mg of 7-hydroxymethyl-4-isopropyl-2-[3-(N-methyl-N-phenethylamino)propoxy]-2,4,6-cycloheptatrien-1-one as a yellowish brown oil (yield: 74%).

$^1$H NMR (CDCl$_3$) δ(ppm) 1.27 (d, 6H, J=6.8 Hz), 2.10 (qui, 2H, J=6.5 Hz), 2.34 (m, 3H), 2.6–2.9 (7H), 4.07 (t, 2H, J=6.5 Hz), 4.66 (s, 2H), 6.78 (s, 1H), 6.83 (d, 1H, J=9.5 Hz), 7.1–7.3 (5H), 7.46 (d, 1H, J=9.5 Hz).

7-hydroxymethyl-4-isopropyl-2-[3-(N-methyl-N-phenethylamino)propoxy]-2,4,6-cycloheptatrien-1-one (242 mg, 0.655 mmol) and triethylamine (0.11 ml, 0.789 mmol) were dissolved in dichloromethane (1 ml), to which was added methanesulfonyl chloride (61 μl, 0.788 mmol) at room temperature for 5 hours, the solvent was distilled off under reduced pressure. 1-(4,4'-difluorobenzhydryl)piperazine (230 mg, 0.798 mmol) and triethylamine (0.11 ml, 0.789 mmol) were added to the residue, and the resultant was dissolved in chloroform (5 ml). The solution was heated and refluxed for 16 hours, diluted with dichloromethane, washed with water and dried over sodium sulfate. After the solvent was distilled off under reduced pressure, the residue was purified by silica gel column chromatography [eluent:chloroform/methanol (30:1)] to give 156 mg of 7-difluorobenzhydryl)piperazino-1-methyl]-4-isopropyl-2-[3-N-methyl-N-phenethylamino)propoxy]-2,4,6-cycloheptatrien-1-one as a yellowish brown oil (yield: 37%).

MS m/z 639 (M$^+$)

$^1$H NMR (CDCl$_3$) δ(ppm) 1.24 (d, 6H, J=6.8 Hz), 2.07 (qui, 2H, J=6.5 Hz), 2.32 (s, 3H), 2.40 (m, 4H), 2.54 (m, 4H), 2.3–2.9 (6H), 3.62 (s, 2H), 4.03 (t, 2H, J=6.5 Hz), 4.23 (1H), 66.69 (s, 1H), 6.78 (d, 1H, J=9.2 Hz), 6.96 (t, 4H, J=8.9 Hz), 7.1–7.3 (5H), 7.34 (dd, 4H, J=8.9, 5.4 Hz), 7.63 (d, 1H, J=9.2 Hz).

EXAMPLE 16

Production of 7-[4-(4-chlorobenzhydryl)piperazino-1-methyl]-2-methoxy-2,4,6-cycloheptatrien-1-one Tropolone (1 g, 8.0 mmol) and 4-(4-chlorobenzhydryl)piperazine (2.82 g, 9.6 mmol) were dissolved in methanol (40 ml), to which were added 37% formalin (800 mg, 9.6 mmol) and acetic acid (590 mg, 9.6 mmol), and the resultant was stirred at 60° C. for an hour. Water was added to the solution which was extracted with chloroform, dried over sodium sulfate and concentrated under reduced pressure. The resulting residue was purified by silica gel column chromatography [eluent:chloroform/methanol (100:1)] to give 600 mg of 7-[4-(4-chlorobenzhydryl)piperazino-1methyl]-2-hydroxy-2,4,6-cycloheptatrien-1-one as a pale yellowish brown amorphous powder (yield: 18%).

MS m/z 420 (M$^+$)

$^1$H NMR (CDCl$_3$) δ(ppm) 2.4–2.6 (8H) 3.73 (s, 2H), 4.24 (s, 1H), 7.04 (m, 1H), 7.2–7.4 (11H), 7.85 (d, 1H, J=9.7 Hz).

7-[4-(4-chlorobenzhydryl)piperazino-1-methyl]-2-hydroxy-2,4,6-cycloheptatrien-1-one (200 mg, 0.47 mmol) was dissolved in acetone (50 ml), to which were added potassium carbonate (263 mg, 1.9 mmol) and dimethyl sulfate (78 mg, 0.62 mmol) and the resultant was heated and refluxed for an hour. Water was added to the solution, which was extracted with chloroform, dried over sodium sulfate and concentrated under reduced pressure. The resulting residue was purified by silica gel column chromatography [eluent:chloroform/methanol (100:1)] to give 20 mg of 7-[4-(4-chlorobenzhydryl)piperazino-1-methyl]-2-methoxy-2,4,6-cycloheptatrien-1-one as a pale brown amorphous powder (yield: 10%).

MS m/z 434 (M$^+$)

$^1$H NMR (CDCl$_3$) δ(ppm) 2.4–2.6 (8H), 3.67 (s, 1H), 3.92 (s, 3H), 4.23 (s, 1H), 6.72 (d, 1H, J=9.5 Hz), 6.90 (bt, 1H, J=9.7 Hz), 7.03 (bt, 1H, J=9.7 Hz), 7.2–7.4 (9H), 7.76 (d, 1H, J=9.7 Hz).

EXAMPLE 1B

Production of 2-(2'-oxo-3'-methoxy-5'-isopropyl-3',5',7'-cycloheptatrienyl)-3-phenethylbenzothiazoline (1aB) Benzothiazolin-2-one (5.15 g, 34.1 mmol) was dissolved in dimethylformamide (100 ml) and to the solution was added 60% sodium hydride (1.36 g, 34.1 mmol) which was stirred at room temperature until generation of hydrogen gas stopped. Then β-phenylethylbromide (4.89 ml, 35.8 mmol) was added to the solution which was stirred at room temperature for 17 hours. To the reaction solution was added a saturated aqueous solution of ammonium chloride, followed by extraction with ethyl acetate. The organic layer was washed in turn with a saturated sodium bicarbonate solution and saline and dried over anhydrous sodium sulfate. The solvent was distilled off under reduced pressure. The crude product thus obtained was purified by subjecting it to silica gel column chromatography to give 6.49 g of 3-phenethylbenzothiazoline-2-one as a white amorphous powder form n-hexane/ethyl (4:1)-eluted fraction (yield: 80%).

$^1$H NMR (CDCl$_3$) δ(ppm) 5.16 (2H, s), 6.96 (1H, dd, J=8.1 Hz), 7.13 (1H, ddd, J=8, 8, 1 Hz), 7.27–7.36 (5H, m), 7.43 (1H, ddd, J=8, 1 Hz).

(1bB) 3-phenethylbenzothiazolin-2-one (2.0 g, 7.83 mmol) was heated at reflux in ethanol (90 ml)/potassium hydroxide (10.0 g) under nitrogen atmosphere for 17 hours. After cooling, the reaction solution was neutralized with hydrochloric acid and dried over anhydrous magnesium sulfate, and then the solvent was distilled off under reduced pressure to give 2-(2-phenyl)ethylaminothiophenol. This was dissolved in toluene (18 ml) and to the solution was added 7-formyl-14-isopropyl-2-methoxy-2,4,6-cycloheptatrien-1-one (1.63 g, 7.90 mmol), followed by heating at reflux for 17 hours under nitrogen atmosphere. The reaction solution was concentrated under reduced pressure and the crude product was purified by subjecting it to silica gel column chromatography to obtain 2.04 g of 2-(2'-oxo-3'-methoxy-5'-isopropyl-3',5',7'-cycloheptatrienyl)-3-phenethylbenzothiazoline as a blown amorphous powder from toluene/acetone (6:1)—eluted fraction (yield: 62%).

$^1$H NMR (CDCl$_3$) δ(ppm) 1.25 (6H, d, J=7 Hz), 2.77–2.97 (3H, m), 3.22 (1H, ddd, J=15, 10, 6 Hz), 3.69 (1H, ddd, J=15, 10, 6 Hz), 3.97 (3H, s), 6.43 (1H, s), 6.61 (1H, d, J=8 Hz), 6.69 (1H ddd, J=8, 8, 1 Hz), 6.74 (1H, s), 6.80 (1H, d, J=10 Hz), 6.69–7.03 (2H, m), 7.13–7.30 (5H, m), 7.48 (1H, d, J=10 Hz).

MS (m/e): 417 (M$^+$, 35%), 412 (100%), 312 (17%)

EXAMPLES 2aB TO 14aB

According to the same reaction operation as that of Example 1a, various N-substituted benzothiaozolines were synthesized. The results are shown in Table 7 below.

TABLE 7
| Ex. No. | Alkylating agent | N-substituted benzothiazolinone | Yield(%) | $^1$H-NMR(CDCl$_3$)δ(ppm) = |
|---|---|---|---|---|
| 2aB | MeI | 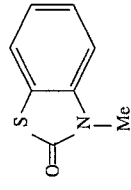 | 98 | 3.46(3H, S), 7.04(1H, d, J=8Hz), 7.17(1H, ddd, J=8, 8, 1Hz), 7.33(1H, ddd, J=8, 8, 1Hz), 7.43(1H, dd, J=8, 1Hz). |
| 3aB | 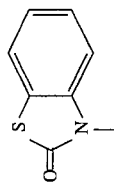 | 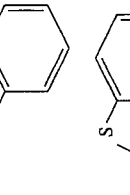 | 79 | 5.16(2H, S), 6.96(1H, dd, J=8, 1Hz), 7.13(1H, ddd, J=8, 8, 1Hz), 7.22(1H, ddd, J=8, 8, 1Hz), 7.26–7.36(5H, m), 7.43(1H, dd, J=8, 1Hz) |
| 4aB | 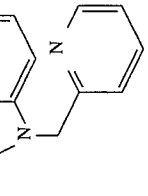 | 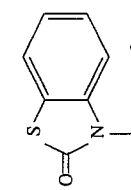 | 75 | 5.28(2H, S), 7.10–7.23(5H, m), 7.43(1H, dd, J=8, 1Hz), 7.63(1H, ddd, J=8, 8, 2Hz), 8.57(1H, d, J=5Hz) |
| 5aB | 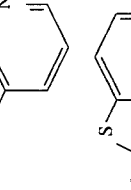 | 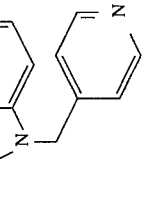 | 67 | 5.16(2H, S), 6.96(1H, dd, J=8, 1Hz), 7.16(1H, ddd, J=8, 8, 1Hz), 7.22–7.28(2H, m), 7.45(1H, dd, J=7, 1Hz), 7.62(1H, ddd, J=8, 8, 2Hz), 8.54(1H, dd, J=5, 2Hz), 8.64(1H, d, J=2Hz) |
| 6aB |  |  | 51 | 5.15(2H, S), 6.85(1H, d, J=8Hz), 7.15–7.27(4H, m), 7.47(1H, d, J=7Hz), 8.58(1H, m) |

TABLE 7-continued

| Ex. No. | Alkylating agent | N-substituted benzothiazolinone | Yield(%) | $^1$H-NMR(CDCl$_3$)δ(ppm) = |
|---|---|---|---|---|
| 7aB | 2-(2-pyridyl)ethyl tosylate | N-[2-(2-pyridyl)ethyl]benzothiazolin-2-one | 70 | 3.20(2H, t, J=8Hz), 4.35(2H, t, J=8Hz), 7.07–7.16(4H, m), 7.25(1H, ddd, J=8, 8, 1Hz), 7.40(1H, dd, J=8, 1Hz), 7.55(1H, ddd, J=8, 8, 2Hz), 8.58(1H, ddd, J=8, 4, 1Hz) |
| 8aB | 2-(3,4-dimethoxyphenyl)ethyl tosylate | N-[2-(3,4-dimethoxyphenyl)ethyl]benzothiazolin-2-one | 58 | 2.98(2H, t, J=8Hz), 3.81(3H, S), 3.85(3H, S), 4.14(2H, t, J=8Hz), 6.68(1H, S), 6.74–6.84(2H, m), 6.95(1H, d, J=8Hz), 7.14(1H, ddd, J=8, 8, 1Hz), 7.28(1H, ddd, J=8, 8, 1Hz), 7.43(1H, dd, J=8, 2Hz) |
| 9aB | 2-(chloromethyl)quinoline hydrochloride | N-[(quinolin-2-yl)methyl]benzothiazolin-2-one | 45 | 5.46(2H, S), 7.12(1H, ddd, J=8, 5, 4Hz), 7.16–7.20(2H, m), 7.35(1H, d, J=8Hz), 7.43(1H, d, J=7Hz), 7.55(1H, dd, J=7, 7Hz), 7.74(1H, dd, J=8, 1Hz), 7.79(1H, dd, J=8Hz), 8.10(2H, d, J=8Hz) |
| 10aB | N-methyl-N-(2-phenylethyl)-3-chloropropylamine | N-[3-(N-methyl-N-(2-phenylethyl)amino)propyl]benzothiazolin-2-one | 64 | 1.89(2H, qui, J=7Hz), 2.30(3H, S), 2.46(2H, t, J=7Hz), 2.60(2H, dd, J=10, 6Hz), 2.77(2H, dd, J=10, 6Hz), 3.94(2H, t, J=7Hz), 7.05(1H, d, J=8Hz), 7.14(1H, ddd, J=8, 8, 1Hz), 7.17–7.20(3H, m), 7.26–7.31(3H, m), 7.42(1H, dd, J=8, 1Hz) |

TABLE 7-continued

| Ex. No. | Alkylating agent | N-substituted benzothiazolinone | Yield(%) | $^1$H-NMR(CDCl$_3$)δ(ppm) = |
|---|---|---|---|---|
| 11aB (Note 1) |  | 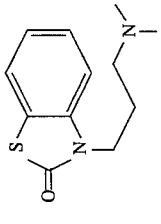 | 52 | 2.33(6H, S), 2.62(2H, t, J=7Hz), 4.06(2H, t, J=7Hz), 7.08(1H, d, J=8Hz), 7.16(1H, ddd, J=8, 8, 1Hz), 7.43(1H, dd, J=8, 1Hz) |
| 12aB (Note 1) | 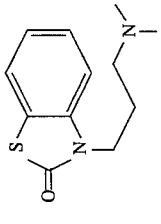 | 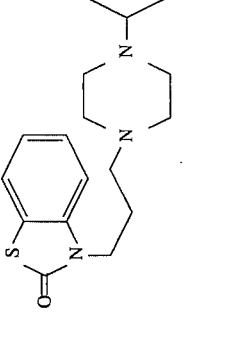 | 55 | 1.90(2H, qui, J=7Hz), 2.23(6H, S), 2.34(2H, t, J=7Hz), 4.01(2H, t, J=7Hz), 7.15(1H, d, J=8Hz), 7.15(1H, dd, J=8, 8Hz), 7.31(1H, ddd, J=8, 8, 1Hz), 7.43(1H, dd, J=8, 1Hz) |
| 13aB (Note 2) | | 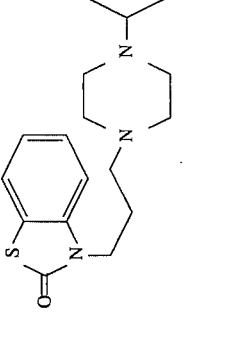 | 85 | 1.90(2H, quintet, J=7Hz), 2.40(10H, bt like), 3.99(2H, t, J=7Hz), 4.20(1H, S), 6.96(4H, t, J=9Hz), 7.13(2H, t like), 7.25–7.36(5H, m), 7.40(1H, d, J=9Hz) |

Note 1:
Sodium ethoxide solution was used in place of sodium hydride.

Note 2:
By using 1,3-dibromopropane, according to the same manner as that of Example 1(a), 3-(3-bromopropyl)benzothiazoline-2-one was obtained in a yield of 64%. The resulting bromo compound was heated at reflux with 4-(4,4'-difluorobenzhydryl)piperadine in toluene under the existence of potassium carbonate to obtain the N-substituted benzothiazolinone compound 13(a) in a yield of 85%.

EXAMPLES 2bB TO 14bB

According to the same reaction operation as that of Example 1(b), various compounds [Ia] were synthesized. The results are shown in Table 8.

TABLE 2

| Ex. No. | Compound [Ia] | Yield(%) | $^1$H NMR(CDCl$_3$) δ(ppm) = | MS (m/e) |
|---|---|---|---|---|
| 2bB | (structure: 2-(N-methyl-N-phenylamino)methylthio substituted methoxy-isopropyl tropone) | 65 | 1.27(6H, d, J=7Hz), 2.88(3H, S) 2.89(1H, m), 3.97(3H, S), 6.37(1H, S), 6.49(1H, d, J=8Hz), 6.67(1H, ddd, J=8,8,1Hz), 6.75(1H, S), 6.86(1H, d, J=10Hz), 6.96(1H, d, J=8Hz), 6.99(1H, dd, J=8,8Hz), 7.56(1H, d, J=10Hz) | 327(M$^+$, 33%) 312(100%) 284(100%) |
| 3bB | (structure: 2-(N-benzyl-N-phenylamino)methylthio substituted methoxy-isopropyl tropone) | 10 | 1.25(6H, d, J=7Hz), 2.85(1H, m), 3.94(3H, S), 4.22(1H, d, J=16Hz), 4.67(1H, d, J=16Hz), 6.44(1H, S), 6.60(1H, d, J=8Hz), 6.69(1H, ddd, J=8,8, 1Hz), 6.72(1H, br.S), 6.81(1H, d, J=10Hz), 6.95(1H, ddd, J=8,8, 1Hz), 7.00(1H, dd, J=8, 1Hz), 7.21–7.28(5H, m), 7.56(1H, d, J=10Hz) | 403(M$^+$, 2%) 388(2%) 312(100%) 284(35%) |
| 4bB | (structure: 2-(N-(2-pyridylmethyl)-N-phenylamino)methylthio substituted methoxy-isopropyl tropone) | 8 | 1.23(6H, d, J=7Hz), 2.83(1H, m), 3.88(3H, S), 4.85(2H, S), 5.98(1H, br.S), 6.50(1H, d, J=8Hz), 6.63(1H, d, J=2Hz), 6.81(1H, dd, J=8, 8Hz), 6.88–6.93(3H, m), 7.02(1H, dd, J=8, 2Hz), 7.19(1H, m), 7.55(1H, d, J=8Hz), 7.65(1H, ddd, J=8,8, 2Hz), 8.59(1H, d, J=5Hz) | 404(M$^+$, 54%) 312(100%) |

TABLE 2-continued

| Ex. No. | Compound [Ia] | Yield(%) | $^1$H NMR(CDCl$_3$) δ(ppm) = | MS (m/e) |
|---|---|---|---|---|
| 5bB | (structure: methoxy-isopropyl-tropone with S-CH linked to N(phenyl)(CH$_2$-3-pyridyl)) | 9 | 1.22(6H, d, J=7Hz), 2.83(1H, m), 3.87(3H, S), 4.76(2H, S), 5.89(1H, S), 6.51(1H, d, J=8Hz), 6.62(1H, d, J=2Hz), 6.81–6.99(3H, m), 6.89(1H, S), 7.04(1H, dd, J=7, 2Hz), 7.26–7.30(1H, m), 7.80(1H, d, J=8Hz), 8.52(1H, dd, J=5, 2Hz), 8.66(1H, d, J=2Hz) | 404(M$^+$, 54%) 313(37%) 312(100%) |
| 6bB | (structure: methoxy-isopropyl-tropone with S-CH linked to N(phenyl)(CH$_2$-3-pyridyl)) | 41 | 1.23(6H, d, J=7Hz), 2.84(1H, m), 3.88(3H, S), 4.74(2H, S), 5.90(1H, br.S), 6.39(1H, d, J=8Hz), 6.63(1H, d, J=2Hz), 6.84–6.93(3H, m), 6.87(1H, S), 7.04(1H, dd, J=7.2Hz), 7.36(2H, d, J=6Hz), 8.57(2H, d, J=6Hz) | 404(M$^+$, 40%) 312(100%) |
| 7bB | (structure: methoxy-isopropyl-tropone with S-CH linked to N(phenyl)(CH$_2$CH$_2$-2-pyridyl)) | 26 | 1.23(6H, d, J=7Hz), 2.82(1H, m), 3.22(2H, m), 3.88(2H, m), 3.89(3H, S), 6.62(1H, d, J=2Hz), 6.76(1H, d, J=8Hz), 6.80–6.85(2H, m), 6.81(1H, S), 6.99(1H, dd, J=8.2Hz), 7.04(1H, dd, J=8, 8Hz), 7.15(1H, dd, J=8, 5Hz), 7.29(1H, d, J=8Hz), 7.62(1H, ddd, J=8, 8, 2Hz), 8.57(1H, d, J=5Hz) | |

TABLE 2-continued

| Ex. No. | Compound [Ia] | Yield(%) | $^1$H NMR(CDCl$_3$) δ(ppm) = | MS (m/e) |
|---|---|---|---|---|
| 8bB | (structure) | 34 | 1.25(6H, d, J=7Hz), 2.79–2.89(3H, m), 3.19(1H, m), 3.70(1H, m), 3.83(3H, S), 3.84(3H, S), 3.97(3H, S), 6.42(1H, S), 6.59(1H, d, J=8Hz), 6.66–6.82(6H, m), 6.98(1H, d, J=7Hz), 6.99(1H, dd, J=8, 8Hz), 7.46(1H, d, J=10Hz) | 477(M$^+$, 36%) 462(54%) 312(19%) 165(100%) |
| 9bB | (structure) | 25 | 1.25(6H, d, J=7Hz), 2.82(1H, m), 3.88(3H, S), 5.01(2H, S), 6.54(2H, m), 6.62(1H, d, J=7Hz), 6.72–8.24(11H, m) | |
| 10bB | (structure) | 14 | 1.25(6H, d, J=7Hz), 1.74(2H, m), 2.26(3H, S), 2.41(2H, m), 2.52–2.58(2H, m), 2.73(2H, m), 2.84(1H, m), 3.00(1H, m), 2.48(1H, m), 3.96(3H, S), 6.41(1H, S), 6.56(1H, d, J=8Hz), 6.65(1H, dd, J=7, 7Hz), 6.73(1H, S), 6.82(1H, d, J=9Hz), 6.95(1H, d, J=7Hz), 6.96(1H, dd, J=8Hz), 7.14–7.26(5H, m), 7.45(1H, d, J=10Hz) | 488(M$^+$, 45%) 473(9%) 312(61%) 176(98%) |

TABLE 2-continued

| Ex. No. | Compound [1a] | Yield(%) | ¹H NMR(CDCl₃) δ(ppm) = | MS (m/e) |
|---|---|---|---|---|
| 11bB | (structure: 2-methoxy-5-isopropyl-tropone with CH(SPh)- substituent bearing N(CH₂CH₂NMe₂)(2-thiophenyl-like aryl)) | 17 | 1.26(6H, d, J=7Hz), 2.22(6H, S), 2.44-2.55(2H, m), 2.86(1H, m), 3.17(1H, m), 3.55(1H, m), 3.97(3H, S), 6.44(1H, S), 6.60(1H, d, J=8Hz), 6.67(1H, dd, J=8, 8Hz), 6.74(1H, S), 6.84(1H, d, J=9Hz), 6.96(1H, d, J=7Hz), 6.98(1H, dd, J=7, 7Hz), 7.51(1H, d, J=10Hz) | |
| 12bB | (structure: analogous with propyl linker to NMe₂) | 2 | 1.25(6H, d, J=7Hz), 1.78(2H, m), 2.22(6H, S), 2.35(2H, m), 2.85(1H, m), 3.08(1H, m), 3.55(1H, m), 3.96(3H, S), 6.42(1H, S), 6.60(1H, d, J=8Hz), 6.66(1H, dd, J=7, 7Hz), 6.74(1H, S), 6.83(1H, d, J=10Hz), 6.95-6.99(2H, m), 7.48(1H, d, J=10Hz) | |
| 13bB | (structure: tropone derivative with piperazine linker bearing bis(4-fluorophenyl)methyl group) | 36 | 1.24(6H, d, J=7Hz), 1.80(2H, m), 2.40(10H, br.t), 2.83(1H, m), 3.07(1H, m), 3.54(1H, m), 3.95(3H, S), 4.20(1H, S), 6.24(1H, S), 6.58(1H, d, J=8Hz), 6.65(1H, dd, J=8, 7Hz), 6.73(1H, S), 6.81(1H, d, J=10Hz), 6.93-6.99(6H, m), 7.30-7.35(4H, m), 7.46(1H, d, J=10Hz) | |

TABLE 2-continued

| Ex. No. | Compound [Ia] | Yield(%) | $^1$H NMR(CDCl$_3$) δ(ppm) = | MS (m/e) |
|---|---|---|---|---|
| 14bB (Note 1) | (structure) | 5 | 1.27(6H, d, J=7Hz), 2.85(3H, S), 2.91(1H, m), 6.51(1H, d, J=8Hz), 6.54(1H, S), 6.71(1H, dd, J=7Hz), 6.98–7.05(3H, m), 7.35(1H, S), 7.79(1H, d, J=10Hz) | |

Note 1: 7-formyl-4-isopropyl-2-hydroxy-2,4,6-cycloheptatriene-1-one was used as aldehide.

EXAMPLE 15B

Production of 2-[2'-oxo-3'-(1-piperazinyl)-5'-isopropyl-3',5',7'-cycloheptatrienyl]-3-phenethylbenzothiazoline 2-(2'-oxo-3'-methoxy-5'-isopropyl-3',5',7'-cycloheptatrienyl)-3-phenethylbenzothiazoline (compound 1b) (100 mg, 0.24 mmol) was heated at reflux with piperazine (31 mg, 0.36 mmol) in toluene (6 ml) for 3.5 hours. The reaction solution was concentrated under reduced pressure and the resulting crude product was purified by subjecting it to silica gel thin-layer chromatography (developing solvent: chloroform/methanol=10/1) to obtain 105 mg of 2-(2'-oxo-3'-(1-piperazinyl-5'-isopropyl-3',5',7'-cycloheptatrienyl)-3-phenethylbenzothiazolineasanorangeviscose liquid (yield: 93%).

$^1$H NMR (CDCl$_3$) δ(ppm) 1.22 (6H, d, J=7 Hz), 2.71 (1H, br s), 2.80 (1H, m), 2.88 (2H, m), 3.17 (4H, br s), 3.22 (1H, m), 3.34 (4H, br s), 3.70 (1H, m), 6.38 (1H, s), 6.59 (1H, d, J=8 Hz), 6.65–6.74 (3H, m), 6.97 (2H, d, J=8 Hz), 7.14–7.30 (5H, m), 7.40 (1H, d, J=10 Hz).

EXAMPLE 16B

Production of 2-{2'-oxo-3'-[2-(N,N-dimethylamino)-ethyl]-5'-isopropyl-3',5',7'-cycloheptatrienyl]}-3-phenethylbenzothiazoline A solution of compound 1b (100 mg, 0.24 mmol) and N,N-dimethyl-ethylenediamine (36 mg, 0.41 mmol) in toluene (6 ml) was refluxed for 2.5 hours. The reaction solution was concentrated under reduced pressure and the resulting crude product was purified by subjecting it to silica gel thin-layer chromatography [developing solvent:chloroform/methanol (10:1)] to obtain 82.5 mg of 2-(2'-oxo-3'-[2-(N,N-diethylamino)ethyl]amino-5'-isopropyl-3',5',7'-cycloheptatrienyl)-3-phenethylbenzothiazoline as a yellow amorphous powder (yield: 73%).

$^1$H NMR (CDCl$_3$) δ(ppm) 1.26 (6H, d, J=7 Hz), 2.32 (6H, s), 2.68 (2H, m), 2.38–2.94 (3H, m), 3.22 (1H, m), 3.37 (2H, m), 3.68 (1H, m), 6.53 (1H, s), 6.59 (1H, t, J=8 Hz), 6.64–6.70 (2H, m), 6.98 (2H, d, J=7 Hz), 7.15–7.13 (6H, m), 7.55 (1H, d, J=10 Hz), 7.77 (1H, br s).

EXAMPLE 17B

Production of 2-(2'-oxo-3'-methoxy-5'-isopropyl-3',5',7'-cycloheptatrienyl)-3-phenethyl-1,1-dioxobenzothiazoline The compound 1b (50 mg, 0.12 mmol) was dissolved in chloroform (10 ml) and the mixture was cooled to 0' C. To this was added m-chloroperbenzoic acid (83 mg, 0.48 mmol) which was stirred at 0° C. for 17 hours. To the reaction solution was added saturated aqueous sodium bicarbonate solution, followed by extraction with ethyl acetate. The organic layer was washed with saline and dried over anhydrous sodium sulfate, and the solvent was distilled off under reduced pressure. The resulting residue was purified by subjecting it to silica gel chromatography to obtain 36 mg of 2-(2'-oxo-3'-methoxy-5'-isopropyl-3',5',7'-cycloheptatrienyl)-3-phenethyl-1,1-dioxobenzothiazoline as a blown amorphous powder from toluene/acetone (4:1)-eluted fraction (yield: 66%).

$^1$H NMR (CDCl$_3$) δ(ppm) 1.26 (6H, d, J=7 Hz), 2.83–2.92 (3H, m), 3.27 (1H, m), 3.82 (1H, m), 3.99 (3H, s), 6.17 (1H, s), 6.73–6.94 (2H, m), 7.13–7.29 (6H, m), 7.47 (1H, ddd, J=8, 8, 1 Hz), 7.57 (1H, dd, J=8, 1 Hz).

MS (m/e): 449 (M$^+$, 13%), 342 (100%), 105 (64%), 91 (89%)

EXAMPLE 18B

Production of 2-(2'-oxo-3'-methoxy-5'-isopropyl-3',5',7'-cycloheptatrienyl)-3-phenethyl-1-oxobenzothiazoline The compound 1b (52 mg, 0.13 mmol) was dissolved in chloroform (5 ml) and the mixture was cooled to 0° C. To this was added m-chloroperbenzoic acid (22.9 mg, 0.13 mmol) which was stirred for 3 hours. To the reaction solution was added saturated aqueous sodium bicarbonate solution, followed by extraction with ethyl acetate. The organic layer was washed with saline and dried over anhydrous sodium sulfate, and the solvent was distilled off under reduced pressure. The resulting residue was purified by subjecting it to silica gel chromatography to obtain 49 mg of 2-(2'-oxo-3'-methoxy-5'-isopropyl-3',5',7'-cycloheptatrienyl)-3-phenethyl-1-oxo-benzothiazoline as a blown amorphous powder from toluene/acetone (1:1)-eluted fraction (yield: 90%).

$^1$H NMR (CDCl$_3$) δ(ppm) 1.25 (6H, d, J=7 Hz), 2.77 (6H, s), 2.83 (1H, m), 3.95 (3H, s), 4.27 (2H, s), 6.68–6.71 (2H, m), 6.94 (1H, m), 7.03–7.16 (3H, m), 7.52 (1H, d, J=10 Hz).

EXAMPLE 1C

Production of 7-[4-(4,4'-difluorobenzhydryl)piperazino-1-methyl]-2-(N-2-dimethylaminoethylamino)-4-isopropyl-2,4,6-cycloheptatrien-1-one 7-[4-(4,4'-difluorobenzhydryl)piperazino-1-methyl]-4-isopropyl-2-methoxy-2,4,6-cycloheptatrien-1-one (130 mg, 0.27 mmol) and N,N-dimethylethylenediamine (0.05 ml, 0.46 mmol) were dissolved in toluene (5 ml) and the resulting solution was heated at reflux for 6 hours. After the solvent was distilled off under reduced pressure, the residue was purified by subjecting it to silica gel column chromatography [eluent:chloroform/methanol (50:1 to 30:1)] to give 71 mg of 7-[4-(4,4'-difluorobenzhydryl)piperazino-1-methyl]-2-(N-2-dimethylaminoethylamino)-4-isopropyl-2,4,6-cycloheptatrien-1-one as a yellowish brown amorphous powder (yield: 49%).

MS m/z 534 (M$^+$)

$^1$H NMR (CDCl$_3$) δ(ppm) 1.27 (6H, d, J=6.8 Hz), 2.41 (4H, m), 2.56 (4H, m), 2.65 (2H, t, J=6.0 Hz), 2.85 (1H, qui, J=6.8 Hz), 3.34 (2H, q, J=6.0 Hz), 3.70 (2H, s), 4.23 (1H, s), 6.46 (1H, s), 6.61 (1H, d, J=9.6 Hz), 6.95 (4H, t, J=8.6 Hz), 7.33 (4H, dd, J=8.6 and 5.5 Hz), 7.61 (1H, d, J=9.6 Hz), 7.67 (1H, broad t).

EXAMPLE 2C

Production of 7-[4-(4,4'-difluorobenzhydryl)piperazino-1-methyl]-2-(N-3-dimethylaminopropylamino)-4-isopropyl-2,4,6-cycloheptatrien-1-one 7-[4-(4,4'-difluorobenzhydryl)piperazino-1-methyl]-4-isopropyl-2-methoxy-2,4,6-cycloheptatrien-1-one (153 mg, 0.32 mmol) and N,N-dimethyl-1,3-propanediamine (0.08 ml, 0.64 mmol) were dissolved in toluene (2 ml) and the resulting solution was heated at reflux for 5 hours. After the solvent was distilled off under reduced pressure, the residue was purified by subjecting it to silica gel column chromatography [eluent:chloroform/methanol (10:1)] to give 124 mg of 7-[4-(4,4'-difluorobenzhydryl)piperazino-1-methyl]-2-(N-3-dimethylaminopropylamino)-4-isopropyl-2,4,6-cycloheptatrien-1-one as a yellowish brown amorphous powder (yield: 71%).

MS m/z 548 (M$^+$)

¹H NMR (CDCl₃) δ(ppm) 1.26 (6H, d, J=6.8 Hz), 1.90 (2H, qui, J=6.8 Hz), 2.25 (6H, s), 2.42 (2H, t, J=6.8 Hz), 2.42 (4H, m), 2.57 (4H, m), 2.86 (1H, qui, J=6.8 Hz), 3.37 (2H, q, J=6.8 Hz), 3.70 (2H, s), 4.23 (1H, s), 6.51 (1H, s), 6.62 (1H, d, J=10.0 Hz), 6.95 (4H, t, J=8.7 Hz), 7.34 (4H, dd, J=8.7 and 5.4 Hz), 7.53 (1H, broad t), 7.62 (1H, d, J=10.0 Hz).

EXAMPLE 3C

Production of 7-[4-(4,4'-difluorobenzhydryl)piperazino-1-methyl]-4-isopropyl-2-(N-2-methylaminoethylamino)-2,4,6-cycloheptatrien-1-one 7-[4-(4,4'-difluorobenzhydryl)piperazino-1-methyl]-4-isopropyl-2-methoxy-2,4,6-cycloheptatrien-1-one (228 mg, 0.48 mmol) and N-methylethylenediamine (0.063 ml, 0.72 mmol) were dissolved in toluene (2 ml) and the resulting solution was heated at reflux for 5 hours. After the solvent was distilled off under reduced pressure, the residue was purified by subjecting it to silica gel preparative thin-layer chromatography [developing solvent:chloroform/methanol (10:1), twice developing] to give 88 mg of 7-[4-(4,4'-difluorobenzhydryl)piperazino-1-methyl]-4-isopropyl-2-(N-2-methylaminoethylamino)-2,4,6-cycloheptatrien-1-one as a yellowish brown amorphous powder (yield: 35%).

MS m/z 520 (M⁺)

¹H NMR (CDCl₃) δ(ppm) 1.26 (6H, d, J=6.8 Hz), 2.45 (4H, m), 2.51 (3H, s), 2.63 (4H, m), 2.89 (1H, qui, J=6.8 Hz), 3.00 (2H, t, J=5.9 Hz), 3.49 (2H, q, J=5.9 Hz), 3.76 (2H, s), 4.24 (1H, s), 6.54 (1H, s), 6.64 (1H, d, J=10.3 Hz), 6.95 (4H, t, J=8.9 Hz), 7.33 (4H, dd, J=8.9 and 5.4 Hz), 7.61 (1H, broad t), 7.66 (1H, d, J=10.3 Hz).

EXAMPLE 4C

Production of 2-(N-2-aminoethylamino)-7-[4-(4,4'-difluorobenzhydryl)piperazino-1-methyl]-4-isopropyl-2,4,6-cycloheptatrien-1-one 7-[4-(4,4'-difluorobenzhydryl)piperazino-1-methyl]-4-isopropyl-2-methoxy-2,4,6-cycloheptatrien-1-one (185 mg, 0.39 mmol) and ethylenediamine (0.077 ml, 1.15 mmol) were dissolved in toluene (2 ml) and the resulting solution was heated at reflux for 5 hours. After the solvent was distilled off under reduced pressure, the residue was purified by subjecting it to silica gel column chromatography [eluent:chloroform/methanol (10:1)—chloroform/methanol/aqueous ammonia (5:1:0.1)] to give 142 mg of 2-(N-2-aminoethylamino)-7-[4-(4,4'-difluorobenzhydryl)piperazino-1-methyl]-4-isopropyl-2,4,6-cycloheptatrien-1-one as a yellowish brown amorphous powder (yield: 72%).

MS m/z 506 (M⁺)

¹H NMR (CDCl₃) δ(ppm) 1.26 (6H, d, J=6.8 Hz), 2.41 (4H, m), 2.57 (4H, m), 2.86 (1H, qui, J=6.8 Hz), 3.07 (2H, t, J=6.0 Hz), 3.40 (2H, q, J=6.0 Hz), 3.70 (2H, s), 4.23 (1H, s), 6.53 (1H, s), 6.64 (1H, d, J=9.7 Hz), 6.96 (4H, t, J=8.6 Hz), 7.34 (4H, dd, J=8.6 and 5.4 Hz), 7.54 (1H, broad t), 7.63 (1H, d, J=9.7 Hz).

EXAMPLE 5C

Production of 7-[4-(4,4'-difluorobenzhydryl)piperazino-1-methyl]-2-(N-2-dimethylaminoethyl-N-methylamino)-4-isopropyl-2,4,6-cycloheptatrien-1-one 7-[4-(4,4'-difluorobenzhydryl)piperazino-1-methyl]-4-isopropyl-2-methoxy-2,4,6-cycloheptatrien-1-one (151 mg, 0.32 mmol) and N,N,N'-trimethylethylenediamine (0.08 ml, 0.63 mmol) were dissolved in toluene (2 ml) and the resulting solution was heated at reflux for 5 hours. After the solvent was distilled off under reduced pressure, the residue was purified by subjecting it to silica gel chromatography [eluent:chloroform/methanol (10:1)] to give 148 mg of 7-[4-(4,4'-difluorobenzhydryl)piperazino-1-methyl]-2-(N-2-dimethylaminoethyl-N-methylamino)-4-isopropyl-2,4,6-cycloheptatrien-1-one as a yellowish brown oily product (yield: 85%).

MS m/z 543 (M⁺)

¹H NMR (CDCl₃) δ(ppm)1.21 (6H, d, J=6.8 Hz), 2.25 (6H, s), 2.38 (4H, m), 2.53 (4H, m), 2.55 (2H, t, J=7.3 Hz), 2.76 (1H, qui, J=6.8 Hz), 3.01 (3H, s), 3.52 (2H, t, J=7.3 Hz), 3.59 (2H, s), 4.21 (1H, s), 6.43 (1H, s), 6.46 (1H, d, J=9.2 Hz), 6.95, (4H, t, J=8.8 Hz), 7.33 (4H, dd, J=8.8 and 5.4 Hz), 7.36 (1H, d, J=9.2 Hz).

EXAMPLE 6C

Production of 7-[4-(4,4'-difluorobenzhydryl)piperazino-1-methyl]-2-(N-2-dimethylaminoethyl-N-ethylamino)-4-isopropyl-2,4,6-cycloheptatrien-1-one 7-[4-(4,4'-difluorobenzhydryl)piperazino-1-methyl]-4-isopropyl-2-methoxy-2,4,6-cycloheptatrien-1-one (150 mg, 0.31 mmol) and N,N-dimethyl-N'-ethylethylenediamine (0.1 ml, 0.64 mmol) were dissolved in toluene (2 ml) and the resulting solution was heated at reflux for 12 hours. After the solvent was distilled off under reduced pressure, the residue was purified by subjecting it to silica gel column chromatography [eluent:chloroform/methanol (10:1)] to give 157 mg of 7-[4-(4,4'-difluorobenzhydryl)piperazino-1-methyl]-2-(N-2-dimethyl-N-ethylamino)-4-isopropyl-2,4,6-cycloheptatrien-1-one as a yellowish brown oily product (yield: 89%).

MS m/z 562 (M⁺)

¹H NMR (CDCl₃) δ(ppm) 1.18 (3H, t, J=7.0 Hz), 1.21 (6H, 3, J=7.0 Hz), 2.29 (6H, s), 2.38 (4H, m), 2.53 (4H, m), 2.55 (2H, t, J=7.2 Hz), 3.51 (2H, t, J=7.0 Hz), 3.58 (2H, s), 4.21 (1H, s), 6.42 (1H, d, J=9.7 Hz), 6.44 (1H, s), 6.95 (4H, t, J=8.7 Hz), 7.33 (4H, dd, J=8.7 and 5.7 Hz), 7.33 (1H, d, J=9.7 Hz).

EXAMPLE 7C

Production of 2-(N-2-diethylaminoethylamino)-7-[4-(4,4'-difluorobenzhydryl)piperazino-1-methyl]-4-isopropyl-2,4,6-cycloheptatrien-1-one 7-[4-(4,4'-difluorobenzhydryl)piperazino-1-methyl]-4-isopropyl-2-methoxy-2,4,6-cycloheptatrien-1-one (150 mg, 0.31 mmol) and N,N-diethylethylenediamine (0.088 ml, 0.63 mmol) were dissolved in toluene (2 ml) and the resulting solution was heated at reflux for 4 hours. After the solvent was distilled off under reduced pressure, the residue was purified by subjecting it to silica gel column chromatography [eluent:chloroform/methanol (10:1)] to give 141 mg of 2-(N-2-diethylaminoethylamino)-7-[4-(4,4'-difluorobenzhydryl)piperazino-1-methyl]-4-isopropyl-2,4,6-cycloheptatrien-1-one as a yellowish brown amorphous powder (yield: 80%).

MS m/z 562 (M⁺)

¹H NMR (CDCl₃) δ(ppm) 1.06 (6H, d, J=7.3 Hz), 1.27 (6H, d, J=6.8 Hz), 2.42 (4H, m), 2.57 (4H, m), 2.60 (4H, q, J=7.3 Hz), 2.79 (2H, t, J=6.3 Hz), 2.85 (1H, qui, J=6.8 Hz), 3.33 (2H, q, J=6.3 Hz), 3.71 (2H, s), 4.23 (1H, s), 6.48 (1H, s), 6.61 (1H, d, J=10.3 Hz), 6.95 (4H, t, J=8.7 Hz), 7.34 (4H, dd, J=8.7 and 5.4 Hz), 7.62 (1H, d, J=10.3 Hz), 7.67 (1H, broad t).

EXAMPLE 8C

Production of 2-[N-2-(N'-2-aminoethylamino)ethylamino]-7-[4-(4,4'-difluorobenzhydryl)piperazino-1-methyl]-4-isopropyl-2,4,6-cycloheptatrien-1-one 7-[4-(4,4'-difluorobenzhydryl)piperazino-1-methyl]-4-isopropyl-2-methoxy-2,4,6-cycloheptatrien-1-one (162 mg, 0.34 mmol) and diethylenetriamine (0.073 ml, 0.68 mmol) were dissolved in toluene (2 ml) and the resulting solution was heated at reflux for 7 hours. After the solvent was distilled off under reduced pressure, the residue was purified by subjecting it to silica gel column chromatography [eluent:chloroform/methanol (10:1)—chloroform/methanol/ aqueous ammonia (4:1:0.1)] to give 141 mg of 2-[N-2-(N'-2-aminoethylamino)ethylamino]-7-[4-(4,4'-difluorobenzhydryl)piperazino-1-methyl]-4-isopropyl-2,4,6-cycloheptatrien-1-one as a yellowish brown oily product (yield: 76%).

MS m/z 549 (M$^+$)

$^1$H NMR (CDCl$_3$) δ(ppm) 1.26 (6H, d, J=6.8 Hz), 2.41 (4H, m), 2.56 (4H, m), 2.72 (2H, m), 2.81 (2H, m), 2.85 (1H, qui, J=6.8 Hz), 3.01 (2H, t, J=5.9 Hz), 3.42 (2H, q, J=5.9 Hz), 3.69 (2H, s), 4.23 (1H, s), 6.51 (1H, s), 6.63 (1H, d, J=10.3 Hz), 6.95 (4H, t, J=8.5 Hz), 7.34 (4H, dd, J=8.5 and 5.7 Hz), 7.60 (1H, broad t), 7.62 (1H, d, J=10.3 Hz).

EXAMPLE 9C

Production of 7-[4-(4,4'-difluorobenzhydryl)piperazino-1-methyl]-4-isopropyl-2-[N-2-(2-pyridylamino)ethylamino]-2,4,6-cycloheptatrien-1-one 7-[4-(4,4'-difluorobenzhydryl)piperazino-1-methyl]-4-isopropyl-2-methoxy-2,4,6-cycloheptatrien-1-one (153 mg, 0.32 mmol) and N-(2-pyridyl)ethylenediamine (226 mg, 1.65 mmol) were dissolved in toluene (2 ml) and the resulting solution was heated at reflux for 12 hours. After the solvent was distilled off under reduced pressure, the residue was purified by subjecting it to silica gel column chromatography [eluent:chloroform/methanol (50:1)] to give 180 mg of 7-[4-(4,4'-difluorobenzhydryl)piperazino-1-methyl]-4-isopropyl-2-[N-2-(2-pyridylamino)ethylamino]-2,4,6-cycloheptatrien-1-one as a yellowish brown amorphous powder (yield: 96%).

MS m/z 583 (M$^+$)

$^1$H NMR (CDCl$_3$) δ(ppm) 1.25 (6H, d, J=6.9 Hz), 2.41 (4H, m), 2.56 (4H, m), 2.82 (1H, qui, J=6.9 Hz), 3.62 (2H, m), 3.69 (2H, s), 3.72 (2H, m), 4.23 (1H, s), 4.72 (1H, broad t), 6.39 (1H, d, J=8.4 Hz), 6.57–6.66 (3H), 6.95 (4H, t, J=8.9 Hz), 7.31–7.41 (5H), 7.62 (1H, d, J=10.0 Hz), 7.64 (1H, broad t), 8.14 (1H, d, J=3.5 Hz).

EXAMPLE 10C

Production of 7-[4-(4,4'-difluorobenzhydryl)piperazino-1-methyl]-4-isopropyl-2-[N-2-(2-pyrimidylamino)ethylamino]-2,4,6-cycloheptatrien-1-one 7-[4-(4,4'-difluorobenzhydryl)piperazino-1-methyl]-4-isopropyl-2-methoxy-2,4,6-cycloheptatrien-1-one (156 mg, 0.33 mmol) and N-(2-pyrimidyl)ethylenediamine (108 mg, 0.78 mmol) were dissolved in toluene (2 ml) and the resulting solution was heated at reflux for 12 hours. After the solvent was distilled off under reduced pressure, the residue was purified by subjecting it to silica gel column chromatography [eluent:chloroform/methanol (10:1)] to give 159 mg of 7-[4-(4,4'-difluorobenzhydryl)piperazino-1-methyl]-4-isopropyl-2-[N-2-(2-pyrimidylamino)ethylamino]-2,4,6-cycloheptatrien-1-one as a yellowish brown amorphous powder (yield: 84%).

MS m/z 584 (M$^+$)

$^1$H NMR (CDCl$_3$) δ(ppm) 1.27 (6H, d, J=6.8 Hz), 2.41 (4H, m), 2.56 (4H, s), 284 (1H, qui, J=6.8 Hz), 3.61 (2H, m), 3.69 (2H, s), 3.75 (2H, m), 4.23 (1H, s), 5.62 (1H, broad t), 6.57 (1H, t, J=4.8 Hz), 6.64 (1H, d, J=10.3 Hz), 6.70 (1H, s), 6.95 (4H, t, J=8.8 Hz), 7.34 (4H, dd, J=8.8 and 5.4 Hz), 7.62 (1H, d, J=10.3 Hz), 7.71 (1H, broad t), 8.31 (1H, d, J=4.8 Hz).

Example 11C

Production of 7-[4-(4,4'-difluorobenzhydryl)piperazino-1-methyl]-4-isopropyl-2-[N-2-(2-pyridyl)ethylamino]-2,4,6-cycloheptatrien-1-one 7-[4-(4,4'-difluorobenzhydryl)piperazino-1-methyl]-4-isopropyl-2-methoxy-2,4,6-cycloheptatrien-1-one (153 mg, 0.32 mmol) and 2-(2-aminoethyl)pyridine (0.077 ml, 0.64 mmol) were dissolved in toluene (2 ml) and the resulting solution was heated at reflux for 12 hours. After the solvent was distilled off under reduced pressure, the residue was purified by subjecting it to silica gel column chromatography [eluent:chloroform/methanol (50:1)] to give 134 mg of 7-[4-(4,4'-difluorobenzhydryl)piperazino-1-methyl]-4-isopropyl-2-[N-2-(2-pyridyl)ethylamino]-2,4,6-cycloheptatrien-1-one as a yellowish brown amorphous powder (yield: 75%).

MS m/z 568 (M$^+$)

$^1$H NMR (CDCl$_3$) δ(ppm) 1.26 (6H, d, J=6.9 Hz), 2.41 (4H, m), 2.55 (4H, m), 2.85 (1H, qui, J=6.9 Hz), 3.20 (2H, t, J=6.6 Hz), 3.68 (2H, s), 3.75 (2H, q, J=6.6 Hz), 4.23 (1H, s), 6.55 (1H, s), 6.62 (1H, d, J=10.0 Hz), 6.95 (4H, t, J=8.7 Hz), 7.16 (1H, dd, J=7.6 and 4.9 Hz), 7.21 (1H, d, J=7.6 Hz), 7.33 (4H, dd, J=8.7 and 5.3 Hz), 7.57 (1H, broad t), 7.59–7.65 (2H), 8.59 (1H, d, J=4.3 Hz).

EXAMPLE 12C

Production of 7-[4-(4,4'-difluorobenzhydryl)piperazino-1-methyl]-4-isopropyl-2-(N-2-pyridylmethylamino)-2,4,6-cycloheptatrien-1-one 7-[4-(4,4'-difluorobenzhydryl)piperazino-1-methyl]-4-isopropyl-2-methoxy-2,4,6-cycloheptatrien-1-one (158 mg, 0.33 mmol) and 2-(2-aminomethyl)pyridine (0.051 ml, 0.50 mmol) were dissolved in toluene (2 ml) and the resulting solution was heated at reflux for 4 hours. After the solvent was distilled off under reduced pressure, the residue was purified by subjecting it to silica gel preparative thin-layer chromatography [eluent:chloroform/methanol (50:1); three times developing] to give 82 mg of 7-[4-(4,4'-difluorobenzhydryl)piperazino-1-methyl]-4-isopropyl-2-(N-2-pyridylmethylamino)-2,4,6-cycloheptatrien-1-one as a yellowish brown amorphous powder (yield: 45%).

MS m/z 554 (M$^+$)

$^1$H NMR (CDCl$_3$) δ(ppm) 1.12 (6H, d, J=6.8 Hz), 2.42 (4H, m), 2.57 (4H, m), 2.76 (1H, qui, J=6.8 Hz), 3.72 (2H, s), 4.23 (1H, s), 4.69 (2H, d, J=5.9 Hz), 6.47 (1H, s), 6.63 (1H, d, J=10.3 Hz), 6.96 (4H, t, J=8.7 Hz), 7.17–7.26 (2H), 7.33 (4H, dd, J=8.7 and 5.3 Hz), 7.62–7.65 (2H), 8.09 (1H, broad t), 8.62 (1H, d, J=4.9 Hz).

EXAMPLE 13C

Production of 7-[4-(4,4'-difluorobenzhydryl)piperazino-1-methyl]-2-(N-2-hydroxyethylamino)-4-isopropyl-2,4,6-cycloheptatrien-1-one 7-[4-(4,4'-difluorobenzhydryl)piperazino-1-methyl]-4-isopropyl-2-methoxy-2,4,6-cycloheptatrien-1-one (265 mg, 0.55 mmol) and 2-aminoethanol (0.05 ml, 0.83 mmol) were dissolved in toluene (2 ml) and the resulting solution was heated at reflux for 12 hours. After the solvent was distilled off under reduced pressure, the residue was purified by subjecting it to silica gel column chromatography [eluent:chloroform/methanol (20:1)] to give 185 mg of 7-[4-(4,4'-difluorobenzhydryl)piperazino-1-methyl]-2-(N-2-hydroxyethylamino)-4-isopropyl-2,4,6-cycloheptatrien-1-one as a yellowish brown amorphous powder (yield: 66%).

MS m/z 507 (M$^+$)

$^1$H NMR (CDCl$_3$) δ(ppm) 1.26 (6H, d, J=6.8 Hz), 2.41 (4H, m), 2.56 (4H, m), 2.86 (1H, qui, J=6.8 Hz), 3.51 (2H, q, J=5.4 Hz), 3.69 (2H, s), 3.94 (2H, t, J=5.4 Hz), 4.23 (1H, s), 6.57 (1H, s), 6.65 (1H, t, J=10.0 Hz), 6.95 (4H, t, J=8.7 Hz), 7.33 (4H, dd, J=8.7 and 5.5 Hz), 7.59 (1H, broad t), 7.63 (1H, d, J=10.0 Hz).

EXAMPLE 14C

Production of 7-[4-(4,4'-difluorobenzhydryl)piperazino-1-methyl]-4-isopropyl-2-(N-2-methoxyethylamino)-2,4,6-cycloheptatrien-1-one 7-[4-(4,4'-difluorobenzhydryl)piperazino-1-methyl]-4-isopropyl-2-methoxy-2,4,6-cycloheptatrien-1-one (161 mg, 0.34 mmol) and 2-methoxyethylamine (0.088 ml, 1.01 mmol) were dissolved in toluene (2 ml) and the resulting solution was heated at reflux for 12 hours. After the solvent was distilled off under reduced pressure, the residue was purified by subjecting it to silica gel column chromatography [eluent:chloroform/methanol (10:1)] to give 115 mg of 7-[4-(4,4'-difluorobenzhydryl)piperazino-1-methyl]-4-isopropyl-2-(N-2-methoxyethylamino)-2,4,6-cycloheptatrien-1-one as a yellowish brown amorphous powder (yield: 66%).

MS m/z 521 (M$^+$)

$^1$H NMR (CDCl$_3$) δ(ppm) 1.26 (6H, d, J=6.8 Hz), 2.41 (4H, m), 2.57 (4H, m), 2.85 (1H, qui, J=6.8 Hz), 3.41 (3H, s), 3.49 (2H q, J=5.6 Hz), 3.69 (2H, t, J=5.6 Hz), 3.70 (2H, s), 4.23 (1H, s), 6.52 (1H, s), 6.63 (1H, d, J=10.3 Hz), 6.95 (4H, t, J=8.6 Hz), 7.33 (4H, dd, J=8.6 and 5.4 Hz), 7.54 (1H, broad t), 7.62 (1H, d, J=10.3 Hz).

EXAMPLE 15C

Production of methyl 2-{N-7-[4-(4,4'-difluorobenzhydryl)piperazino-1-methyl]-4-isopropyl-1-oxo-2,4,6-cycloheptatrien-2-ylamino}acetate 7-[4-(4,4'-difluorobenzhydryl)piperazino-1-methyl]-4-isopropyl-2-methoxy-2,4,6-cycloheptatrien-1-one (159 mg, 0.33 mmol), glycine methyl ester hydrochloride (83 mg, 0.66 mmol) and diisopropylethylamine (0.11 ml, 0.63 mmol) were dissolved in toluene (2 ml) and the resulting solution was heated at reflux for 5 hours. After the solvent was distilled off under reduced pressure, the residue was diluted with dichloromethane, washed with 2N NaOH, dried over anhydrous sodium sulfate and then concentrated under reduced pressure. The residue was purified by subjecting it to silica gel column chromatography [eluent:chloroform/methanol (50:1)] to give 52 mg of methyl 2-{N-7-[4-(4,4'-difluorobenzhydryl)piperazino-1-methyl]-4-isopropyl-1-oxo-2,4,6-cycloheptatrien-2-ylamino}acetate as a yellowish brown amorphous powder (yield: 29%).

MS m/z 535 (M$^+$)

$^1$H NMR (CDCl$_3$) δ(ppm) 1.25 (6H, d, J=7.0 Hz), 2.43 (4H, m), 2.57 (4H, m), 2.85 (1H, qui, J=7 Hz), 3.70 (2H, s), 3.81 (3H, s), 4.10 (2H, d, J=5.7 Hz), 4.23 (1H, s), 6.31 (1H,s), 6.68 (1H, d, J=8.6 Hz), 6.96 (4H, t, J=8.7 Hz); 7.34 (4H, dd, J=8.7 and 5.5 Hz), 7.67 (1H, d, J=8.6 Hz), 7.69 (1H, broad t).

EXAMPLE 16C

Production of ethyl 3-{N-7-[4-(4,4'-difluorobenzhydryl)piperazino-1-methyl ]-4-isopropyl-1-oxo-2,4,6-cycloheptatrien-2-ylamino}propionate 7-[4-(4,4'-difluorobenzhydryl)piperazino-1-methyl]-4-isopropyl-2-methoxy-2,4,6-cycloheptatrien-1-one (159 mg, 0.33 mmol), β-alanine ethyl ester hydrochloride (98 mg, 0.64 mmol) and diisopropylethylamine (0.11 ml, 0.63 mmol) were dissolved in toluene (2 ml) and the resulting solution was heated at reflux for 12 hours. After the solvent was distilled off under reduced pressure, the residue was diluted with dichloromethane, washed with 2N NaOH, dried over anhydrous sodium sulfate and then concentrated under reduced pressure. The residue was purified by subjecting it to silica gel column chromatography [eluent:chloroform/methanol (50:1)] to give 154 mg of ethyl 2-{N-7-[4-(4,4'-difluorobenzhydryl)piperazino-1-methyl]-4-isopropyl-1-oxo-2,4,6-cycloheptatrien-2-ylamino}propionate as a yellowish brown amorphous powder (yield: 86%).

MS m/z 563 (M$^+$)

$^1$H NMR (CDCl$_3$) δ(ppm) 1.27 (6H, d, J=6.8 Hz), 1.27 (3H, t, J=7.2 Hz), 2.41 (4H, m), 2.56 (4H, m), 2.72 (2H, t, J=6.7 Hz), 2.87 (1H, qui, J=6.8 Hz), 3.65 (2H, q, J=6.7 Hz), 3.69 (2H, s), 4.18 (2H, q, J=7.2 Hz), 4.23 (1H, s), 6.51 (1H, s), 6.65 (1H, d, J=10.3 Hz), 6.95 (4H, t, J=8.6 Hz), 7.34 (4H, dd, J=8.6 and 5.4 Hz), 7.45 (1H, broad t), 7.64 (1H, d, J=10.3 Hz).

EXAMPLE 17C

Production of 7-[4-(4,4'-difluorobenzhydryl)piperazino-1-methyl]-4-isopropyl-2-piperidino-2,4,6-cycloheptatrien-1-one 7-[4-(4,4'-difluorobenzhydryl)piperazino-1-methyl]-4-isopropyl-2-methoxy-2,4,6-cycloheptatrien-1-one (100 mg, 0.21 mmol) and piperidine (0.031 ml, 0.31 mmol) were dissolved in toluene (2 ml) and the resulting solution was heated at reflux for 12 hours. After the solvent was distilled off under reduced pressure, the residue was purified by subjecting it to silica gel column chromatography [eluent:chloroform/methanol (50:1)] to give 68 mg of 7-[4-(4,4'-difluorobenzhydryl)piperazino-1-methyl]-4-isopropyl-2-piperazino-2,4,6-cycloheptatrien-1-one as a yellowish brown amorphous powder (yield: 61%).

MS m/z 531 (M$^+$)

$^1$H NMR (CDCl$_3$) δ(ppm) 1.22 (6H, d, J=6.8 Hz), 1.65 (2H, m), 1.75 (4H, m), 2.39 (4H, m), 2.53 (4H, m), 2.77 (1H, qui, J=6.8 Hz), 3.19 (4H, m), 3.60 (2H, s), 4.22 (1H, s), 6.58 (1H, d, J=9.2 Hz), 6.65 (1H, s), 6.96 (4H, t, J=8.9 Hz), 7.34 (4H, dd, J=8.9 and 5.4 Hz), 7.45 (1H, d, J=9.2 Hz).

EXAMPLE 18C

Production of 7-[4-(4,4'-difluorobenzhydryl)piperazino-1-methyl]-4-isopropyl-2-morpholino-2,4,6-cycloheptatrien-1-one 7-[4-(4,4'-difluorobenzhydryl)piperazino-1-methyl]-4-isopropyl-2-methoxy-2,4,6-cycloheptatrien-1-one (213 mg, 0.45 mmol) and morpholine (0.058 ml, 0.67 mmol) were dissolved in toluene (2 ml) and the resulting solution was heated at reflux for 12 hours. After the solvent was distilled off under reduced pressure, the residue was purified by subjecting it to silica gel column chromatography [eluent:chloroform/methanol (50:1)] to give 157 mg of 7-[4-(4, 4'-difluorobenzhydryl)piperazino-1-methyl]-4-isopropyl-2-morpholino-2,4,6-cycloheptatrien-1-one as a yellowish brown amorphous powder (yield: 66%).

MS m/z 533 (M$^+$)

$^1$H NMR (CDCl$_3$) δ(ppm) 1.23 (6H, d, J=6.9 Hz), 2.39 (4H, m), 2.53 (4H, m), 2.79 (1H, qui, J=6.9 Hz), 3.22 (4H, m), 3.58 (2H, s), 3.90 (4H, m), 4.22 (1H, s), 6.62 (1H, s), 6.67 (1H, d, J=9.2 Hz), 6.96 (4H, t, J=8.9 Hz), 7.34 (4H, dd, J=8.9 and 5.4 Hz), 7.61 (1H, broad t), 7.50 (1H, d, J=9.2 Hz).

EXAMPLE 19C

Production of 7-[4-(4,4'-difluorobenzhydryl)piperazino-1-methyl]-4-isopropyl-2-(1-piperadino)-2,4,6-cycloheptatrien-1-one 7-[4-(4,4'-difluorobenzhydryl)piperazino-1-methyl]-4-isopropyl-2-methoxy-2,4,6-cycloheptatrien-1-one (353 mg, 0.74 mmol) and piperazine (140 mg, 1.63 mmol) were dissolved in toluene (2 ml) and the resulting solution was heated at reflux for 12 hours. After the solvent was distilled off under reduced pressure, the residue was purified by subjecting it to silica gel column chromatography [eluent:chloroform/methanol (20:1)] to give 97 mg of 7-[4-(4, 4'-difluorobenzhydryl)piperazino-1-methyl]-4-isopropyl-2-(1-piperadino)-2,4,6-cycloheptatrien-1-one as a yellowish brown amorphous powder (yield: 25%).

MS m/z 532 (M$^+$)

$^1$H NMR (CDCl$_3$) δ(ppm) 1.22 (6H, d, J=6.8 Hz), 2.39 (4H, m), 2.53 (4H, m), 2.78 (1H, qui, J=6.8 Hz), 3.07 (4H, m), 3.18 (4H, m), 3.58 (2H, s), 4.22 (1H,s), 6.63 (1H, s), 6.64 (1H, d, J=9.2 Hz), 6.96 (4H, t, J=8.9 Hz), 7.34 (4H, dd, J=8.9 and 5.4 Hz), 7.48 (1H, d, J=9.2 Hz).

EXAMPLE 20C

Production of 7-[4-(4,4'-difluorobenzhydryl)piperazino-1-methyl]-2-[4-(3-ethylamino-2-pyridyl)piperazino]-4-isopropyl-2,4,6-cycloheptatrien-1-one 7-[4-(4,4'-difluorobenzhydryl)piperazino-1-methyl]-4-isopropyl-2-methoxy-2,4,6-cycloheptatrien-1-one (200 mg, 0.42 mmol) and 1-(3-ethylamino-2-pyridyl)piperazine (129 mg, 0.63 mmol) were dissolved in toluene (6 ml) and the resulting solution was heated at reflux for 12 hours. After the solvent was distilled off under reduced pressure, the residue was purified by subjecting it to silica gel column chromatography [eluent:hexane/ethyl acetate (1:1)—hexane/ethyl acetate (3:7)] to give 57 mg of 7-[4-(4,4'-difluorobenzhydryl)piperazino-1-methyl]-2-[4-(3-ethylamino-2-pyridyl)piperazino]-4-isopropyl-2,4,6-cycloheptatrien-1-one as a yellowish brown amorphous powder (yield: 21%).

MS m/z 652 (M$^+$)

$^1$H NMR (CDCl$_3$) δ(ppm) 1.24 (6H, d, J=6.8 Hz), 1.30 (3H, t, J=7.0 Hz), 2.40 (4H, m), 2.54 (4H, m), 2.80 (1H, qui, J=6.8 Hz), 3.15 (2H, m), 3.30 (4H, m), 3.43 (4H, m), 3.61 (2H, s), 4.22 (1H, s), 6.65 (1H, d, J=9.3 Hz), 6.72 (1H, s), 6.83 (1H, dd, J=7.8 and 1.4 Hz), 6.95 (4H, d, J=8.6 Hz), 7.33 (4H, dd, J=8.6 and 5.5 Hz), 7.48 (1H, d, J=9.3 Hz), 7.73 (1H, dd, J=4.9 and 1.4 Hz).

EXAMPLE 21C

Production of 7-[4-(4,4'-difluorobenzhydryl)-2,6-dimethylpiperazino-1-methyl]-4-isopropyl-2-methoxy-2,4,6-cycloheptatrien-1-one 7Chloromethyl-4-isopropyl-2-methoxy-2,4,6-cycloheptatrien-1-one (174 mg, 0.77 mmol) and 1-(4,4'-difluorobenzhydryl)-3,5-dimethylpiperazine (294 mg, 0.93 mmol) and triethylamine (0.13 ml, 0.93 mmol) were dissolved in toluene (5 ml) and the resulting solution was heated at reflux for 12 hours. The reaction solution was diluted with dichloromethane, washed with a saturated aqueous solution of NaHCO$_3$, dried over anhydrous sodium sulfate and then concentrated under reduced pressure. The residue was purified by subjecting it to silica gel column chromatography [eluent:chloroform/methanol (100:1)] to give 66 mg of 7-[4-(4,4'-difluorobenzhydryl)-2,6-dimethylpiperazino-1-methyl]-4-isopropyl-2-methoxy-2,4,6-cycloheptatrien-1-one as a yellowish brown amorphous powder (yield: 17%).

MS m/z 506 (M$^+$)

$^1$H NMR (CDCl$_3$) δ(ppm) 0.74 (6H, d, J=5.9 Hz), 1.27 (6H, d, J=6.8 Hz), 1.76 (2H, t, J=10.8 Hz), 2.68 (2H, d, J=10.8 Hz), 2.76 (2H, m), 2.86 (1H, qui, J=6.8 Hz), 3.74 (2H, s), 3.94 (3H, s), 4.17 (1H, s), 6.72 (1H, s), 6.87 (1H, d, J=9.7 Hz), 6.98 (4H, t, J=8.6 Hz), 7.35 (4H, dd, J=8.6 and 5.7 Hz), 8.09 (1H, d, J=9.7 Hz).

EXAMPLE 22C

Production of 7-[4-(4,4'-difluorobenzhydryl)-2-methylpiperazino-1-methyl]-4-isopropyl-2-methoxy-2,4,6-cycloheptatrien-1-one 7-Chloromethyl-4-isopropyl-2-methoxy-2,4,6-cycloheptatrien-1-one (317 mg, 1.4 mmol), 1-(4,4'-difluorobenzhydryl)-3-methylpiperazine (423 mg, 1.4 mmol) and triethylamine (0.2 ml, 1.43 mmol) were dissolved in chloroform (5 ml) and the resulting solution was heated at reflux for 12 hours. The reaction solution was diluted with dichloromethane, washed with a saturated aqueous solution of NaHCO$_3$, dried over anhydrous sodium sulfate and then concentrated under reduced pressure. The residue was purified by subjecting it to silica gel column chromatography [eluent:hexane/ethyl acetate (2:3)] to give 273 mg of 7-[4-(4,4'-difluorobenzhydryl)-2-methylpiperazino-1-methyl]-4-isopropyl-2-methoxy-2,4,6-cycloheptatrien-1-one as a yellowish brown amorphous powder (yield: 40%).

MS m/z 492 (M$^+$)

$^1$H NMR (CDCl$_3$) δ(ppm) 0.99 (3H, d, J=6.5 Hz), 1.26 (6H, d, J=6.8 Hz), 1.94 (1H, t, J=8.4 Hz), 2.14 (1H, t, J=8.4 Hz), 2.40 (1H, t, J=10.5 Hz), 2.5–2.75 (4H), 2.85 (1H, qui, J=6.8 Hz), 3.49 1H, d, J=17.6 Hz), 3.91 (1H, d, J=17.6 Hz), 3.93 (3H, s), 4.20 (1H, s), 6.70 (1H, s), 6.84 (1H, d, J=9.7 Hz), 6.96 (4H, m), 7.34 (4H, m), 7.80 (1H, d, J=9.7 Hz).

EXAMPLE 23C

Production of 7-[4-(4,4'-difluorobenzhydryl)hexahydro-1H-1,4-diazepin-1-ylmethyl]-4-isopropyl-2-methoxy-2,4,6-cycloheptatrien-1-one 7-Chloromethyl-4-isopropyl-2-methoxy-2,4,6-cycloheptatrien-1-one (250 mg, 1.1 mmol), 1-(4,4'-difluorobenzhydryl)hexahydro-1H-,4-diazepine (667 mg, 2.21 mmol) and triethylamine (0.23 ml, 1.65 mmol) were dissolved in chloroform (15 ml) and the resulting solution was heated at reflux for 12 hours. The reaction solution was diluted with dichloromethane, washed with a saturated aqueous solution of NaHCO$_3$, dried over anhydrous sodium sulfate and then concentrated under reduced pressure. The residue was purified by subjecting it to silica gel column chromatography [eluent:hexane/ethyl acetate (2:3)] to give 108 mg of 7-[4-(4,4'-difluorobenzhydryl)hexahydro-1H-1,4-diazepin-1-yl-methyl]-4-isopropyl-2-methoxy-2,4,6-cycloheptatrien-1-one as a yellowish brown amorphous powder (yield: 20%).

MS m/z 492 (M$^+$)

$^1$H NMR (CDCl$_3$) δ(ppm) 1.28 (6H, d, J=7.0 Hz), 1.77 (2H, m), 2.65–2.95 (9H), 3.79 (2H, s), 3.94 (3H, s), 4.62 (1H, s), 6.70 (1H, s), 6.85 (1H, d, J=10.0 Hz), 6.96 (4H, t, J=8.8 Hz), 7.36 (4H, dd, J=8.8 and 5.4 Hz), 7.78 (1H, d, J=10.0 Hz).

We claim:

1. A tropolone derivative of the formula:

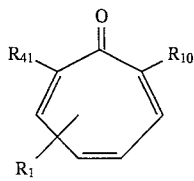

wherein $R_{10}$ is a moiety of the formula III

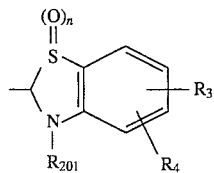 III wherein $R_1$ is:
(a) hydrogen,
(b) $C_1$–$C_5$ alkyl, or
(c) substituted or non-substituted aryl;
wherein $R_3$ and $R_4$ are the same or different and are:
(a) hydrogen,
(b) $C_1$–$C_5$ alkyl,
(c) $C_1$–$C_5$ alkyl substituted by —OH, —COOR$_5$, or —CN,
(d) $C_7$–$C_{20}$ arylalkyl,
(e) halogen,
(f) —OH,
(g) $C_1$–$C_5$ alkoxy,
(h) —CN,
(i) —CO$_2$R$_5$, or
(j) —NO$_2$;
wherein $R_{41}$ is
(a) —OR$_3$,
(b) —OR$_6$,
(c) —NR$_7$R$_8$,
(d) —N(R$_{51}$)—(CH$_2$)$_m$—R$_{61}$, or
(e) a group represented by the formula IV

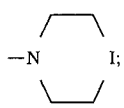 I;

wherein $R_5$ is
(a) hydrogen, or
(b) $C_1$–$C_5$ alkyl;
wherein $R_6$ is
(a) hydrogen, (b) $C_1$–$C_5$ alkyl,
(c) $C_1$–$C_5$ alkyl substituted by OH, COOR$_5$ or CN, or containing O, S, or N as heteroatoms,
(d) $C_7$–$C_{20}$ aralkyl, or
(e) substituted $C_7$–$C_{20}$ aralkyl containing O, S or N as heteroatoms;
wherein $R_7$ and $R_8$ are the same or different and are:
(a) hydrogen,
(b) $C_1$–$C_5$ alkyl,
(c) $C_1$–$C_5$ alkyl substituted by —OH, —COOR$_5$, or —CN, or
(d) $C_7$–$C_{20}$ aralkyl;
wherein $R_9$ is
(a) hydrogen,
(b) $C_1$–$C_5$ alkyl, or
(c) $C_7$–$C_{20}$ aralkyl;
wherein $R_{11}$ is
(a) hydrogen,
(b) $C_1$–$C_3$ alkyl,
(c) substituted or unsubstituted aryl, or
(d) substituted or unsubstituted heterocycle;
wherein $R_{21}$ and $R_{31}$ are the same or different and are
(a) hydrogen, or
(b) $C_1$–$C_3$ alkyl;
wherein $R_{61}$ is
(a) substituted or unsubstituted aryl,
(b) —OR$_{71}$,
(c) —CO$_2$R$_{81}$, or
(d) —NR$_{91}$R$_{101}$;
wherein $R_{51}$, $R_{71}$, and $R_{81}$ are the same or different and are
(a) hydrogen, or
(b) $C_1$–$C_3$ alkyl;
wherein $R_{91}$ and $R_{101}$ are the same or different and are
(a) hydrogen,
(b) $C_1$–$C_3$ alkyl, or
(c) a substituted or unsubstituted aryl group;
wherein $R_{201}$ is
(a) hydrogen,
(b) $C_1$–$C_5$ alkyl,
(c) $C_2$–$C_{20}$ aralkyl, or
(d) $C_6$–$C_{10}$ arylsulfonyl;
wherein X is
(a) —O—,
(b) —CH$_2$—, or
(c) —N((CH$_2$)$_p$—R$_{11}$)—;
wherein m is 1, 2, 3, or 4;
wherein n is 0, 1, or 2;
wherein p is 0, 1, or 2; and
wherein q is 1 or 2;
or a pharmaceutically acceptable ester or salt thereof.

2. A tropolone derivative of claim 1, wherein $R_{41}$ is —OR$_6$ or —NR$_7$R$_8$, $R_{10}$ is a moiety of Formula III, $R_1$ is definitions (a) to (c), $R_3$ and $R_4$ are definitions (a), (b), and (e) to (j) represented by the formula:

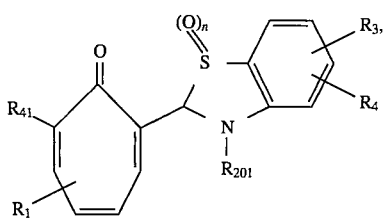

or a pharmaceutically acceptable ester or salt thereof.

3. A compound of claim 2, selected from the group consisting of 2-(2'-oxo-3'-methoxy-5'-isopropyl-3',5',7'-cycloheptatrienyl)-3-phenethylbenzothiazoline;

2-(2'-oxo-3'-methoxy-5'-isopropyl-3',5',7'-cycloheptatrienyl)-3-methylbenzothiazoline;

2-(2'-oxo-3'-methoxy-5'-isopropyl-3',5',7'-cycloheptatrienyl)-3-benzylbenzothiazoline;

2-(2'-oxo-3'-methoxy-5'-isopropyl-3',5',7'-cycloheptatrienyl)-3-(2-picolyl)benzothiazothiazoline;

2-(2'-oxo-3'-methoxy-5'-isopropyl-3',5',7'-cycloheptatrienyl)-3-(3-picolyl)benzothiazoline;

2-(2'-oxo-3'-methoxy-5'-isopropyl-3',5',7'-cycloheptatrienyl)-3-(4-picolyl)benzothiazoline;

2-(2'-oxo-3'-methoxy-5'-isopropyl-3',5',7'-cycloheptatrienyl)-3-[2-pyridyl)ethyl];

2-(2'-oxo-3'-methoxy-5'-isopropyl-3',5',7'-cycloheptatrienyl)-3-[2-(3,4-dimethoxyphenyl)ethyl]benzothiazoline;

2-(2'-oxo-3'-methoxy-5'-isopropyl-3',5',7'-cycloheptatrienyl)-3-(2-quinolyl)methylbenzothiazoline;

2-(2'-oxo-3'-methoxy-5'-isopropyl-3',5',7'-cycloheptatrienyl)-3-[3-(N-methyl-N-phenethylamino)ethyl]benzothiazoline;

2-(2'-oxo-3'-methoxy-5'-isopropyl-3',5',7'-cycloheptatrienyl)-3-[2-(N,N-dimethylamino)ethyl]benzothiazoline;

2-(2'-oxo-3'-methoxy-5'-isopropyl-3',5',7'-cycloheptatrienyl)-3-[2-(N,N-dimethylamino)propyl]benzothiazoline;

2-(2'-oxo-3'-methoxy-5'-isopropyl-3',5',7'-cycloheptatrienyl)-3-{3-(4-(4,4'-difluorobenzhydryl)piperadin-1-yl)propyl}benzothiazoline;

2-(2'-oxo-3'-methoxy-5'-isopropyl-3',5',7'-cycloheptatrienyl)-3-methylbenzothiazoline;

2-(2'-oxo-3'-(1-piperadinyl)-5'-isopropyl-3',5',7'-cycloheptatrienyl)-3-phenethylbenzothiazoline;

2-(2'-oxo-3'-(2-(N,N-dimethyl)aminoethyl)amino-5'-isopropyl-3',5',7'-cycloheptatrienyl)-3-phenethylbenzothiazoline;

2-(2'-oxo-3'-methoxy-5'-isopropyl-3',5',7'-cycloheptatrienyl)-3-(2-phenethyl-1,1-dioxobenzothiazoline; and 2-(2'-oxo-3'-methoxy-5'-isopropyl-3',5',7'-cycloheptatrienyl)-3-phenethyl-1-oxobenzothiazoline.

* * * * *